(12) United States Patent
Hebrank et al.

(10) Patent No.: US 12,285,559 B2
(45) Date of Patent: *Apr. 29, 2025

(54) NASAL DRUG DELIVERY APPARATUS AND METHODS OF USE

(71) Applicant: PNEUMA RESPIRATORY, INC., Boone, NC (US)

(72) Inventors: John H. Hebrank, Durham, NC (US); Christopher W. Maurer, Irvine, CA (US); Charles Eric Hunter, Boone, NC (US); Chengjie Li, Shenzhen (CN); Louis Thomas Germinario, Kingsport, TN (US)

(73) Assignee: PNEUMA RESPIRATORY, INC., Boone, NC (US)

( * ) Notice: Subject to any disclaimer, the term of this patent is extended or adjusted under 35 U.S.C. 154(b) by 265 days.

This patent is subject to a terminal disclaimer.

(21) Appl. No.: 17/957,396

(22) Filed: Sep. 30, 2022

(65) Prior Publication Data
US 2023/0127529 A1    Apr. 27, 2023

Related U.S. Application Data

(63) Continuation of application No. 16/754,885, filed as application No. PCT/US2018/056300 on Oct. 17, 2018, now Pat. No. 11,458,267.
(Continued)

(51) Int. Cl.
*A61M 15/08* (2006.01)
*A61M 15/00* (2006.01)

(52) U.S. Cl.
CPC .......... *A61M 15/08* (2013.01); *A61M 15/002* (2014.02); *A61M 15/009* (2013.01);
(Continued)

(58) Field of Classification Search
CPC .. A61M 15/08; A61M 15/002; A61M 15/009; A61M 2205/0294;
(Continued)

(56) References Cited

U.S. PATENT DOCUMENTS

| 3,934,585 | A | 1/1976 | Maurice |
| 3,970,250 | A | 7/1976 | Drews |

(Continued)

FOREIGN PATENT DOCUMENTS

| AU | 2012258488 | 1/2013 |
| CA | 2364248 | 8/2006 |

(Continued)

OTHER PUBLICATIONS

Copley, "Understanding cascade impaction and its importance for inhaler testing," Copley Scientific, Copley White Paper [serial online], Jul. 2007 [retrieved on May 7, 2017]. Retrieved from the Internet: URL: http://www.copleyscientific.com/files/ww/articles/Understanding%20Cascade%20Impaction%20White%20Paper.pdf; 6 pp.

(Continued)

*Primary Examiner* — Jason E Flick
(74) *Attorney, Agent, or Firm* — Polsinelli PC

(57) ABSTRACT

A nasal droplet delivery device and related methods for delivering precise and repeatable dosages to a subject via the nasal passageways and sinus cavities.

20 Claims, 12 Drawing Sheets

Related U.S. Application Data

Figure 1:
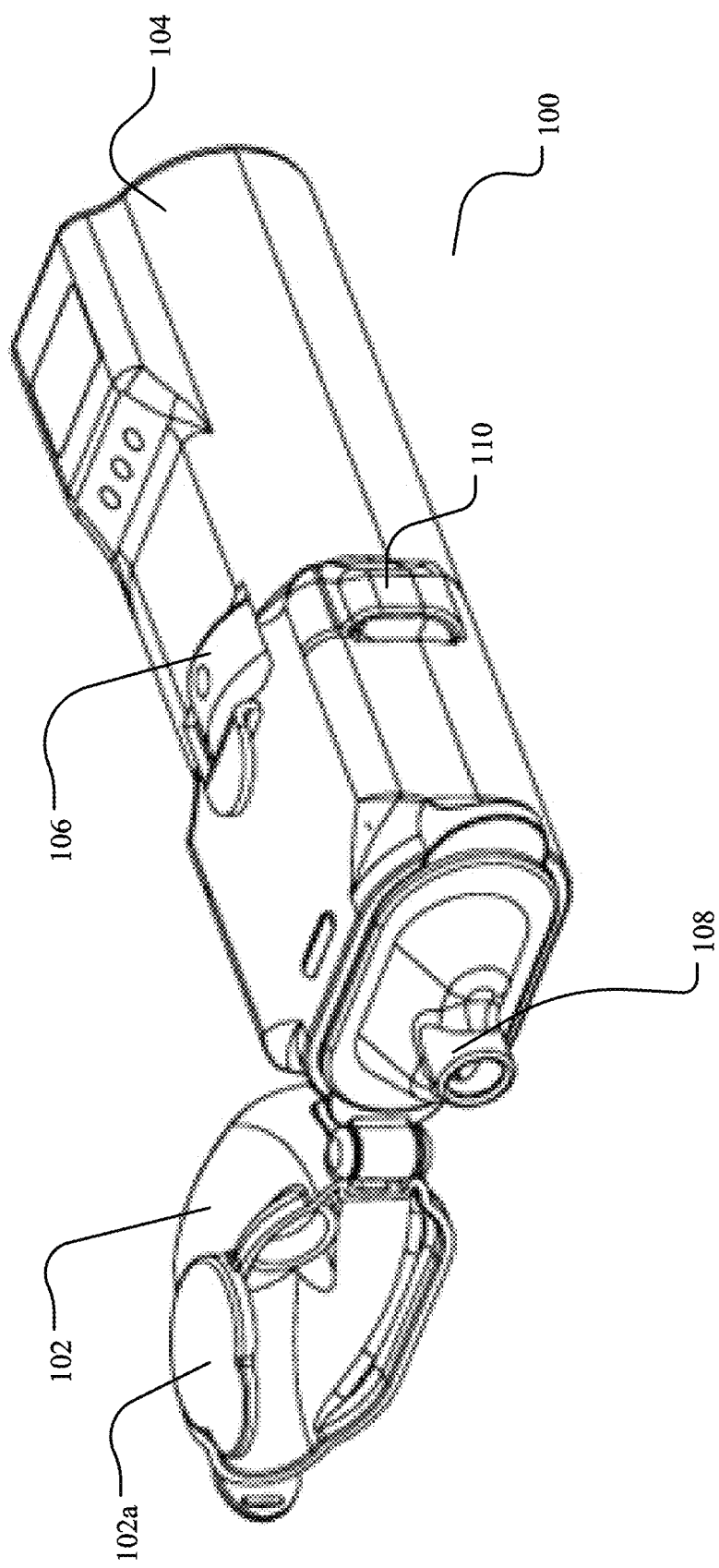
Figure 2:
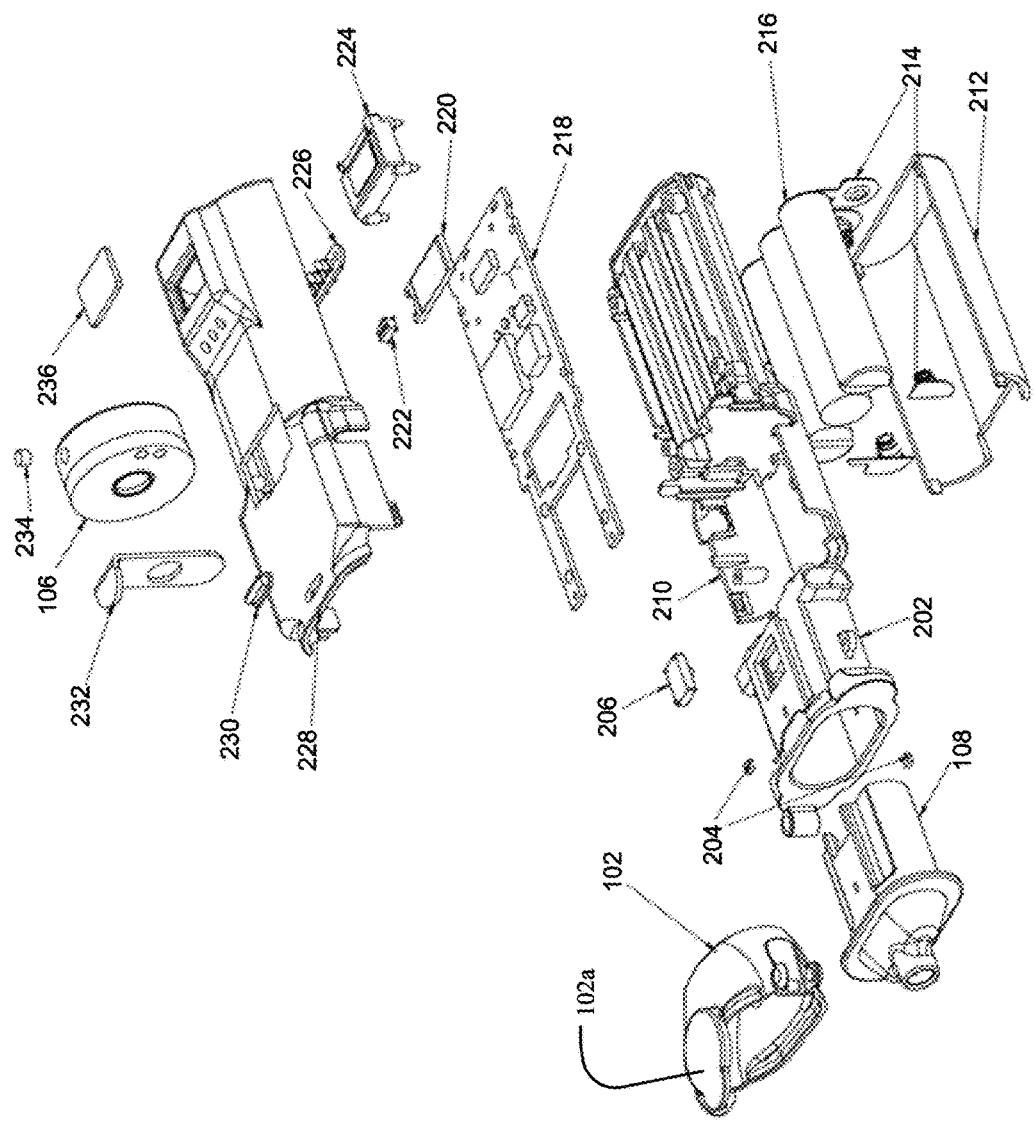

(60) Provisional application No. 62/573,543, filed on Oct. 17, 2017.

(52) U.S. Cl.
CPC . *A61M 2205/0294* (2013.01); *A61M 2205/13* (2013.01); *A61M 2205/3306* (2013.01); *A61M 2205/3313* (2013.01); *A61M 2205/3344* (2013.01); *A61M 2205/584* (2013.01); *A61M 2205/587* (2013.01)

(58) Field of Classification Search
CPC ...... A61M 2205/13; A61M 2205/3306; A61M 2205/3313; A61M 2205/3344; A61M 2205/3592; A61M 15/00; A61M 15/0005; A61M 15/001; A61M 15/0085; A61M 2205/0272; A61M 2205/02; A61M 2205/33; A61M 2205/3331
See application file for complete search history.

(56) References Cited

U.S. PATENT DOCUMENTS

| | | | |
|---|---|---|---|
| 5,021,701 A | 6/1991 | Takahashi et al. | |
| 5,164,740 A | 11/1992 | Ivri | |
| 5,363,842 A | 11/1994 | Mishelevich et al. | |
| 5,487,378 A | 1/1996 | Robertson et al. | |
| 5,497,763 A | 3/1996 | Lloyd et al. | |
| 5,586,550 A | 12/1996 | Ivri et al. | |
| 5,607,410 A | 3/1997 | Branch | |
| 5,630,793 A | 5/1997 | Rowe | |
| 5,758,637 A | 6/1998 | Ivri et al. | |
| 5,826,570 A | 10/1998 | Goodman et al. | |
| 5,828,394 A | 10/1998 | Khuri-Yakub et al. | |
| 5,881,716 A | 3/1999 | Wirch et al. | |
| 5,884,620 A | 3/1999 | Gonda et al. | |
| 5,894,841 A | 4/1999 | Voges | |
| 5,906,202 A | 5/1999 | Schuster et al. | |
| 5,938,117 A | 8/1999 | Ivri | |
| 5,979,247 A | 11/1999 | Kizawa | |
| 6,011,062 A | 1/2000 | Schneider et al. | |
| 6,062,212 A | 5/2000 | Davison et al. | |
| 6,071,498 A | 6/2000 | Narodylo et al. | |
| 6,085,740 A | 7/2000 | Ivri et al. | |
| 6,158,431 A | 12/2000 | Poole | |
| 6,196,219 B1 | 3/2001 | Hess et al. | |
| 6,235,177 B1 | 5/2001 | Borland et al. | |
| 6,443,146 B1 | 9/2002 | Voges | |
| 6,615,826 B1 | 9/2003 | Gabrio et al. | |
| 6,629,524 B1 | 10/2003 | Goodall et al. | |
| 6,637,430 B1 * | 10/2003 | Voges | A61M 15/0065 141/2 |
| 6,896,910 B2 | 5/2005 | Kim et al. | |
| 6,978,941 B2 | 12/2005 | Litherland et al. | |
| 6,981,499 B2 | 1/2006 | Anderson et al. | |
| 7,191,777 B2 | 3/2007 | Brand et al. | |
| 7,198,044 B2 | 4/2007 | Trueba | |
| 7,219,664 B2 | 5/2007 | Ruckdeschel et al. | |
| 7,628,339 B2 | 12/2009 | Ivri et al. | |
| 7,648,957 B2 | 1/2010 | Heyden et al. | |
| 7,708,011 B2 | 5/2010 | Hochrainer et al. | |
| 7,883,031 B2 | 2/2011 | Collins, Jr. et al. | |
| 7,900,625 B2 | 3/2011 | Kleinstreuer et al. | |
| 7,954,486 B2 | 6/2011 | Papania et al. | |
| 7,976,140 B2 | 7/2011 | Umeda | |
| 8,012,136 B2 | 9/2011 | Collins, Jr. et al. | |
| 8,367,734 B1 | 2/2013 | Gao et al. | |
| 8,474,452 B2 | 7/2013 | Gumaste et al. | |
| 8,545,463 B2 | 10/2013 | Collins, Jr. et al. | |
| 8,555,874 B2 | 10/2013 | Fink et al. | |
| 8,684,980 B2 | 4/2014 | Hunter et al. | |
| 8,733,935 B2 | 5/2014 | Ballou, Jr. et al. | |
| 8,753,308 B2 | 6/2014 | Palmer et al. | |
| 8,936,021 B2 | 1/2015 | Collins, Jr. | |
| 8,985,100 B2 | 3/2015 | Minocchieri et al. | |
| 9,087,145 B2 | 7/2015 | Ballou, Jr. et al. | |
| 9,227,029 B2 | 1/2016 | Addington et al. | |
| 9,242,054 B2 | 1/2016 | Fink et al. | |
| 9,352,108 B1 | 5/2016 | Reed et al. | |
| 9,452,274 B2 | 9/2016 | Addington et al. | |
| 9,463,486 B2 | 10/2016 | Wilkerson et al. | |
| 9,539,604 B2 | 1/2017 | Wilkerson et al. | |
| 9,956,360 B2 | 5/2018 | Germinario et al. | |
| 9,962,507 B2 | 5/2018 | Germinario et al. | |
| 10,449,314 B2 | 10/2019 | Germinario et al. | |
| 10,525,220 B2 | 1/2020 | Hunter et al. | |
| 10,568,543 B2 | 2/2020 | Yan | |
| 10,898,666 B2 | 1/2021 | Germinario et al. | |
| 2002/0002975 A1 | 1/2002 | Power | |
| 2002/0032387 A1 | 3/2002 | Geva et al. | |
| 2002/0046750 A1 | 4/2002 | Gonda et al. | |
| 2002/0071871 A1 | 6/2002 | Snyder et al. | |
| 2002/0121274 A1 | 9/2002 | Borland et al. | |
| 2003/0072717 A1 | 4/2003 | Reinhold et al. | |
| 2003/0098022 A1 | 5/2003 | Nakao et al. | |
| 2003/0101991 A1 | 6/2003 | Trueba | |
| 2003/0127538 A1 | 7/2003 | Patel et al. | |
| 2003/0140921 A1 | 7/2003 | Smith et al. | |
| 2003/0150445 A1 | 8/2003 | Power et al. | |
| 2003/0196654 A1 | 10/2003 | Stein | |
| 2003/0205229 A1 | 11/2003 | Crockford et al. | |
| 2004/0009231 A1 | 1/2004 | Jackson et al. | |
| 2004/0139963 A1 | 7/2004 | Ivri et al. | |
| 2004/0195403 A1 | 10/2004 | Atterybury et al. | |
| 2004/0215157 A1 | 10/2004 | Peclat et al. | |
| 2004/0256487 A1 | 12/2004 | Collins, Jr. et al. | |
| 2005/0011514 A1 | 1/2005 | Power et al. | |
| 2005/0077315 A1 | 4/2005 | Pavlu et al. | |
| 2005/0121025 A1 | 6/2005 | Gamard et al. | |
| 2005/0150489 A1 * | 7/2005 | Dunfield | A61M 15/0083 128/200.14 |
| 2005/0172476 A1 | 8/2005 | Stone et al. | |
| 2005/0172958 A1 | 8/2005 | Singer et al. | |
| 2005/0217666 A1 | 10/2005 | Fink et al. | |
| 2005/0224075 A1 * | 10/2005 | Childers | A61M 15/0065 128/200.14 |
| 2005/0236501 A1 | 10/2005 | Zimlich, Jr. et al. | |
| 2007/0023036 A1 | 2/2007 | Grychowski et al. | |
| 2007/0044793 A1 | 3/2007 | Kleinstreuer et al. | |
| 2007/0083677 A1 | 4/2007 | Cecka et al. | |
| 2007/0119969 A1 | 5/2007 | Collins, Jr. et al. | |
| 2007/0125370 A1 | 6/2007 | Denyer et al. | |
| 2007/0157931 A1 | 7/2007 | Parker et al. | |
| 2007/0240714 A1 | 10/2007 | Dunne et al. | |
| 2007/0248645 A1 | 10/2007 | Bague et al. | |
| 2007/0267010 A1 | 11/2007 | Fink et al. | |
| 2008/0000470 A1 | 1/2008 | Minocchieri et al. | |
| 2008/0059228 A1 | 3/2008 | Bossi et al. | |
| 2008/0142010 A1 | 6/2008 | Weaver et al. | |
| 2008/0243050 A1 | 10/2008 | Power et al. | |
| 2008/0271732 A1 * | 11/2008 | Weaver | A61M 15/025 128/200.14 |
| 2008/0283057 A1 | 11/2008 | Rohrschneider et al. | |
| 2008/0295827 A1 | 12/2008 | Kobayashi | |
| 2008/0308096 A1 | 12/2008 | Borgschulte et al. | |
| 2009/0038610 A1 | 2/2009 | Bogh et al. | |
| 2009/0093772 A1 | 4/2009 | Genosar et al. | |
| 2009/0107492 A1 | 4/2009 | Ooida | |
| 2009/0114218 A1 | 5/2009 | Veatch | |
| 2009/0114742 A1 | 5/2009 | Collins, Jr. | |
| 2009/0118243 A1 | 5/2009 | Gjorstrup | |
| 2009/0134235 A1 | 5/2009 | Ivri | |
| 2009/0167812 A1 | 7/2009 | Asai et al. | |
| 2009/0192443 A1 | 7/2009 | Collins, Jr. | |
| 2009/0212133 A1 | 8/2009 | Collins, Jr. | |
| 2009/0235925 A1 | 9/2009 | Power et al. | |
| 2009/0270752 A1 | 10/2009 | Coifman | |
| 2009/0272818 A1 | 11/2009 | Valpey, III et al. | |
| 2009/0314292 A1 | 12/2009 | Overfield et al. | |
| 2009/0317496 A1 | 12/2009 | Park et al. | |
| 2010/0037894 A1 | 2/2010 | Rouse et al. | |
| 2010/0078013 A1 | 4/2010 | Power et al. | |
| 2010/0089395 A1 | 4/2010 | Power et al. | |

(56) References Cited

U.S. PATENT DOCUMENTS

| | | |
|---|---|---|
| 2010/0156995 A1 | 6/2010 | Kanda et al. |
| 2010/0222752 A1 | 9/2010 | Collins, Jr. et al. |
| 2010/0282247 A1 | 11/2010 | Kadrichu et al. |
| 2011/0108025 A1 | 5/2011 | Fink et al. |
| 2011/0114090 A1 | 5/2011 | Piper |
| 2011/0230820 A1 | 9/2011 | Lillis et al. |
| 2011/0253805 A1 | 10/2011 | Lee |
| 2012/0037154 A1 | 2/2012 | Gallem et al. |
| 2012/0048265 A1 | 3/2012 | Smaldone |
| 2012/0266878 A1 | 10/2012 | Watanabe et al. |
| 2012/0291781 A1 | 11/2012 | Kaufmann et al. |
| 2013/0079732 A1 | 3/2013 | Burt et al. |
| 2013/0150812 A1* | 6/2013 | Hunter ............... A61F 9/0026 604/295 |
| 2013/0172830 A1 | 7/2013 | Hunter et al. |
| 2013/0239956 A1 | 9/2013 | Schulz et al. |
| 2013/0267864 A1 | 10/2013 | Addington et al. |
| 2013/0284165 A1 | 10/2013 | Krimsky |
| 2013/0299607 A1 | 11/2013 | Wilkerson et al. |
| 2013/0327323 A1 | 12/2013 | Rubin |
| 2013/0330400 A1 | 12/2013 | Perkins et al. |
| 2013/0334335 A1 | 12/2013 | Wilkerson et al. |
| 2013/0334339 A1 | 12/2013 | Xu |
| 2014/0037735 A1 | 2/2014 | Montgomery |
| 2014/0116426 A1 | 5/2014 | Mullinger et al. |
| 2014/0187969 A1 | 7/2014 | Hunter et al. |
| 2014/0190496 A1 | 7/2014 | Wensley et al. |
| 2014/0213925 A1 | 7/2014 | Chan et al. |
| 2014/0283859 A1 | 9/2014 | Minskoff et al. |
| 2014/0336618 A1 | 11/2014 | Wilkerson et al. |
| 2015/0018694 A1 | 1/2015 | Gomo |
| 2015/0101596 A1 | 4/2015 | Hogan |
| 2015/0136129 A1 | 5/2015 | Mehadevan et al. |
| 2015/0136155 A1 | 5/2015 | Verleur et al. |
| 2015/0164375 A1 | 6/2015 | Schindhelm et al. |
| 2015/0174348 A1 | 6/2015 | Tunnell et al. |
| 2015/0196060 A1 | 7/2015 | Wensley et al. |
| 2015/0273165 A1 | 10/2015 | Hadash |
| 2015/0328151 A1 | 11/2015 | Ballou, Jr. et al. |
| 2015/0352301 A1 | 12/2015 | Stedman et al. |
| 2016/0001018 A1 | 1/2016 | Fink et al. |
| 2016/0001019 A1 | 1/2016 | Fink et al. |
| 2016/0106341 A1 | 4/2016 | Adam et al. |
| 2016/0213866 A1 | 7/2016 | Tan |
| 2016/0245830 A1 | 8/2016 | Mace et al. |
| 2016/0310982 A1 | 10/2016 | Von Hollen |
| 2016/0325055 A1 | 11/2016 | Cameron |
| 2016/0354557 A1 | 12/2016 | McPherson Allnutt et al. |
| 2017/0035924 A1 | 2/2017 | Yang et al. |
| 2017/0039344 A1 | 2/2017 | Bitran et al. |
| 2017/0106153 A1 | 4/2017 | Davidson et al. |
| 2017/0106155 A1 | 4/2017 | Reed et al. |
| 2017/0128677 A1 | 5/2017 | Eilat et al. |
| 2017/0158776 A1 | 6/2017 | Feltquate et al. |
| 2017/0203058 A1 | 7/2017 | Davidson et al. |
| 2017/0203323 A1 | 7/2017 | Gschwind et al. |
| 2017/0224706 A1 | 8/2017 | Surber |
| 2017/0270260 A1 | 9/2017 | Shetty et al. |
| 2017/0274163 A1 | 9/2017 | Oliveras et al. |
| 2017/0304565 A1 | 10/2017 | Allosery |
| 2017/0304566 A1 | 10/2017 | Allosery |
| 2017/0319796 A1 | 11/2017 | Germinario et al. |
| 2017/0319797 A1 | 11/2017 | Germinario et al. |
| 2017/0333646 A1 | 11/2017 | Hemy et al. |
| 2018/0056018 A1 | 3/2018 | Canvin et al. |
| 2018/0116871 A1 | 5/2018 | Hunter et al. |
| 2018/0193175 A1 | 7/2018 | Bluecher et al. |
| 2018/0317557 A1 | 11/2018 | Monsees et al. |
| 2018/0344955 A1 | 12/2018 | Germinario et al. |
| 2018/0369515 A1 | 12/2018 | Germinario et al. |
| 2019/0117907 A1 | 4/2019 | Germinario et al. |
| 2019/0125985 A1 | 5/2019 | Germinario et al. |
| 2019/0125986 A1 | 5/2019 | Germinario et al. |
| 2019/0125987 A1 | 5/2019 | Germinario et al. |
| 2019/0134330 A1 | 5/2019 | Germinario et al. |
| 2019/0358420 A1 | 11/2019 | Hunter et al. |
| 2020/0276398 A1 | 9/2020 | Hebrank et al. |
| 2020/0353186 A1 | 11/2020 | Hebrank et al. |
| 2021/0106772 A1 | 4/2021 | Hebrank et al. |
| 2021/0236745 A1 | 8/2021 | Germinario et al. |
| 2021/0275760 A1 | 9/2021 | Hunter et al. |
| 2022/0001122 A1 | 1/2022 | Hunter et al. |

FOREIGN PATENT DOCUMENTS

| | | |
|---|---|---|
| CN | 1788806 | 6/2006 |
| CN | 104511072 | 4/2015 |
| CN | 204995458 | 1/2016 |
| CN | 205019058 | 2/2016 |
| EP | 2724741 | 4/2014 |
| JP | H11-042219 | 2/1999 |
| JP | 2003-265994 | 9/2003 |
| JP | 2006-68508 | 3/2006 |
| KR | 10-2019-122453 | 10/2019 |
| WO | WO 96/09846 | 4/1996 |
| WO | WO 96/14163 | 5/1996 |
| WO | WO 98/48873 | 11/1998 |
| WO | WO 00/10634 | 3/2000 |
| WO | WO 00/47335 | 8/2000 |
| WO | WO 01/85244 | 11/2001 |
| WO | WO 01/87378 | 11/2001 |
| WO | WO 03/020349 | 3/2003 |
| WO | WO 03/059413 | 7/2003 |
| WO | WO 2004/078025 | 9/2004 |
| WO | WO 2006/013952 | 2/2006 |
| WO | WO 2006/083014 | 8/2006 |
| WO | WO 2007/107160 | 9/2007 |
| WO | WO 2008/056986 | 5/2008 |
| WO | WO 2008/058941 | 5/2008 |
| WO | WO 2008/116165 | 9/2008 |
| WO | WO 2009/012371 | 1/2009 |
| WO | WO 2009/111612 | 9/2009 |
| WO | WO 2010/065452 | 6/2010 |
| WO | WO 2011/083377 | 7/2011 |
| WO | WO 2011/091268 | 7/2011 |
| WO | WO 2011/163272 | 12/2011 |
| WO | WO 2012/026963 | 3/2012 |
| WO | WO 2013/098334 | 7/2013 |
| WO | WO 2013/158352 | 10/2013 |
| WO | WO 2013/158967 | 10/2013 |
| WO | WO 2013/173321 | 11/2013 |
| WO | WO 2015/136529 | 9/2015 |
| WO | WO 2016/001924 | 1/2016 |
| WO | WO 2016/003738 | 1/2016 |
| WO | WO 2017/015303 | 1/2017 |
| WO | WO 2017/056103 | 4/2017 |
| WO | WO 2018/213834 | 11/2018 |
| WO | WO 2019/071008 | 4/2019 |
| WO | WO 2019/219865 | 11/2019 |
| WO | WO 2020/072478 | 4/2020 |
| WO | WO 2020/154497 | 7/2020 |
| WO | WO 2020/227717 | 11/2020 |
| WO | WO 2020/264501 | 12/2020 |

OTHER PUBLICATIONS

Kharitonov, "Exhaled markers of inflammatory lung diseases: ready for routine monitoring?" *Swiss Med Wkly*, 2004; 134: 175-192.

Broeders et al., "Inhalation Profiles in Asthmatics and COPD Patients: Reproducibility and Effect of Instruction," *Journal of Aerosol Medicine*, vol. 16, No. 2, 2003, 131-141.

Taube et al., "Use of a portable device to record maximum inspiratory flow in relation to dyspnea in patients with COPD," *Respiratory Medicine*, 2011, 105, 316-312.

Steller, "Microcontroller Based Diagnostic Smart Inhaler," University of Cincinnati, Dec. 7, 2014, 63 pages.

Carvalho et al., "The function and performance of aqueous aerosol devices for inhalation therapy," Journal of Pharmacy and Pharmacology, vol. 68, No. 5, Apr. 8, 2016, pp. 556-578.

* cited by examiner

NASAL DRUG DELIVERY APPARATUS AND METHODS OF USE

RELATED APPLICATIONS

The present application is a continuation of U.S. patent application Ser. No. 16/754,885, filed Apr. 9, 2020, entitled "NASAL DRUG DELIVERY APPARATUS AND METHODS OF USE," now U.S. Pat. No. 11,458,267, which is a U.S. National Stage Application Filed Under 35 U.S.C. 371 of PCT Application No. PCT/US2018/056300, filed Oct. 17, 2018, entitled "NASAL DRUG DELIVERY APPARATUS AND METHODS OF USE," which claims benefit under 35 U.S.C. § 119 of U.S. Provisional Patent Application No. 62/573,543, filed Oct. 17, 2017, entitled "NASAL DRUG DELIVERY APPARATUS AND METHODS OF USE", the contents of all of which are each herein incorporated by reference in their entireties.

TECHNICAL FIELD

The technical field relates generally to medical devices and more specifically to medical devices for the nasal delivery of drugs for the local and systemic delivery of drugs via the nasal passageways and sinus cavities, to treat a variety of conditions.

BACKGROUND OF THE INVENTION

Nasal sprays and aerosols are becoming increasingly popular methods for drug delivery. The nasal route is a non-invasive way of administering drugs with rapid uptake into the bloodstream and is considered to be important for the systematic delivery of proteins and other macromolecules. For instance, nasal delivery can provide for topical treatment of local diseases in the nose and paranasal sinuses, such as allergic and non-allergic rhinitis and sinusitis. Nasal drug delivery is also an attractive route for needle-free vaccination and for systemic drug delivery. In addition, nasal delivery may help address issues related to poor bioavailability, slow absorption, drug degradation, and adverse events in the gastrointestinal tract and avoids the first-pass metabolism in the liver.

Typical nasal spray devices include unit-dose (single use) devices having syringe-like mechanisms and metered-dose devices intended for multiple use. Unit dose devices are appropriate for delivering certain medicaments such as vaccines, whereas metered-dose devices are more suited to long-term dosage regimes, for example for the treatment of rhinitis. A known metered-dose device comprises a vial containing an aqueous suspension of a suitable medicament. The vial is provided with a manually operated pump adapted to atomize metered doses of the medicament formulation for delivery to the nasal cavity. Examples of this type of nasal spray device include Flonase® (fluticasone propionate, GSK), Nasacort® (triamcinolone acetoinide, Sanofi-Aventis) and Nasonex® (mometasone furoate monohydrate, Schering-Plough).

A major challenge is providing a device that delivers an accurate, consistent, and verifiable dose, with a droplet size that is suitable for successful delivery to the targeted nasal passageways. Dose verification, delivery and inhalation of the correct dose at prescribed times is important. Getting patients to use inhalers correctly is also a major problem. A need exists to insure that patients correctly use inhalers and that they administer the proper dose at prescribed times. Problems emerge when patients misuse or incorrectly administer a dose of their medication. Unexpected consequences occur when the patient stops taking medications, owing to not feeling any benefit, or when not seeing expected benefits or overuse the medication and increase the risk of over dosage. Physicians also face the problem of how to interpret and diagnose the prescribed treatment when the therapeutic result is not obtained.

The present disclosure addresses these and other issues.

SUMMARY OF THE INVENTION

The present disclosure generally relates to a nasal droplet delivery device and method of delivering safe, suitable, and repeatable dosages of ejected droplets to a subject for nasal drug delivery. The nasal droplet delivery device and method is capable of delivering a defined volume of fluid in the form of ejected droplets having properties that deliver an adequate and repeatable high percentage ejection for delivery via the nasal passageways and sinus cavities.

In one aspect, the present disclosure includes and provides a nasal droplet delivery device for delivering an ejected stream of droplets via the nasal passageways and sinus cavities of a subject, the device including a housing, a reservoir (drug chamber) for receiving a volume of fluid, an ejector mechanism in fluid communication with the reservoir and configured to eject a stream of aerosol droplets having an average ejected droplet diameter within a range to deposit at least 50% of the ejected droplets into the nasal passageways and sinus cavities, and to minimize passage of droplets to the pulmonary system during use.

In one aspect, the disclosure relates to an automatically actuated nasal droplet device for delivering a fluid as an ejected stream of droplets to the nasal passageways and sinus cavities of a subject. In certain embodiments, the nasal droplet delivery device is configured in an in-line orientation in that the housing, its internal components, and various device components (e.g., the nosepiece, air inlet flow element, etc.) are orientated in a substantially in-line or parallel configuration (e.g., along the airflow path) so as to form a small, hand-held device.

In certain embodiments, the nasal droplet delivery device may include: a housing; a nosepiece positioned at the airflow exit side of the housing; a reservoir disposed within or in fluid communication with the housing for receiving a volume of fluid; an ejector mechanism in fluid communication with the reservoir, the ejector mechanism comprising a piezoelectric actuator and an aperture plate, the aperture plate having a plurality of openings formed through its thickness and the piezoelectric actuator operable to oscillate the aperture plate at a frequency to thereby generate an ejected stream of droplets, at least one differential pressure sensor positioned within the housing; the at least one differential pressure sensor configured to activate the ejector mechanism upon sensing a pre-determined pressure change within the nosepiece to thereby generate an ejected stream of droplets; the ejector mechanism configured to generate the ejected stream of droplets wherein at least about 50% of the droplets are deposited into the nasal passageways and sinus cavities during use. In some embodiments, the ejector mechanism is configured to generate the ejected stream of droplets wherein at least about 50% of the droplets have an average ejected droplet diameter of greater than about 6 microns, e.g., between about 10 microns and about 20 microns, such that at least about 50% of the mass of the ejected stream of droplets is delivered into the nasal passageways and sinus cavities of a subject during use.

In some aspects, the nasal droplet delivery device further includes an air inlet flow element positioned in the airflow at the airflow entrance of the device and configured to facilitate non-turbulent (i.e., laminar and/or transitional) airflow across the exit side of aperture plate and to provide sufficient airflow to ensure that the ejected stream of droplets flows through the droplet delivery device during use. In some embodiments, the air inlet flow element may be positioned within the nosepiece.

In certain embodiments, the housing and ejector mechanism are oriented such that the exit side of the aperture plate is perpendicular to the direction of airflow and the stream of droplets is ejected in parallel to the direction of airflow. In other embodiments, the housing and ejector mechanism are oriented such that the exit side of the aperture plate is parallel to the direction of airflow and the stream of droplets is ejected substantially perpendicularly to the direction of airflow such that the ejected stream of droplets is directed through the housing at an approximate 90 degree change of trajectory prior to expulsion from the housing.

In certain aspects, the nasal droplet delivery device further includes a surface tension plate between the aperture plate and the reservoir, wherein the surface tension plate is configured to increase contact between the volume of fluid and the aperture plate. In other aspects, the ejector mechanism and the surface tension plate are configured in parallel orientation. In yet other aspects, the surface tension plate is located within 2 mm of the aperture plate so as to create sufficient hydrostatic force to provide capillary flow between the surface tension plate and the aperture plate.

In yet other aspects, the aperture plate of the droplet delivery device comprises a domed shape. In other aspects, the aperture plate may be formed of a metal, e.g., stainless steel, nickel, cobalt, titanium, iridium, platinum, or palladium or alloys thereof. Alternatively, the plate can be formed of suitable material, including other metals or polymers, In other aspects. In certain embodiments, the aperture plate is comprised of, e.g., poly ether ether ketone (PEEK), polyimide, polyetherimide, polyvinylidine fluoride (PVDF), ultra-high molecular weight polyethylene (UHMWPE), nickel, nickel-cobalt, palladium, nickel-palladium, platinum, or other suitable metal alloys, and combinations thereof. In other aspects, one or more of the plurality of openings of the aperture plate have different cross-sectional shapes or diameters to thereby provide ejected droplets having different average ejected droplet diameters.

In yet other aspects, the reservoir of the droplet delivery device is removably coupled with the housing. In other aspects, the reservoir of the droplet delivery device is coupled to the ejector mechanism to form a combination reservoir/ejector mechanism module, and the combination reservoir/ejector mechanism module is removably coupled with the housing.

In other aspects, the nasal droplet delivery device may further include a wireless communication module. In some aspects, the wireless communication module is a Bluetooth transmitter.

In yet other aspects, the nasal droplet delivery device may further include one or more sensors selected from an inferred transmitter, a photodetector, an additional pressure sensor, and combinations thereof.

In one aspect, the disclosure relates to a method for generating and delivering a fluid as an ejected stream of droplets to the nasal passageways and sinus cavities of a subject. The method may comprise: (a) generating an ejected stream of droplets via an automatically actuated nasal droplet delivery device of the disclosure, wherein at least 50% of the ejected droplets are deposited into the nasal passageways and sinus cavities; and (b) delivering the ejected stream of droplets to the nasal passageways and sinus cavities of the subject such that at least about 50% of the mass of the ejected stream of droplets is delivered to nasal passageways and sinus cavities of a subject during use.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the detailed descriptions are to be regarded as illustrative in nature and not restrictive.

BRIEF DESCRIPTION OF THE DRAWINGS

FIG. 1 illustrates perspective views of an exemplary nasal droplet delivery device, in accordance with an embodiment of the disclosure.

FIG. 2 is an exploded view of a nasal droplet delivery device of FIG. 1, in accordance with embodiments of the disclosure.

FIG. 3 is a cross-section view of a nasal droplet delivery device of FIG. 1, in accordance with embodiments of the disclosure.

FIGS. 4A-4B illustrate perspective views of another exemplary nasal droplet delivery device, in accordance with embodiments of the disclosure.

FIG. 5 is an exploded view of a nasal droplet delivery device of FIG. 4A-4B, in accordance with embodiments of the disclosure.

FIG. 6 is a cross section perspective view of a nasal droplet delivery device of FIG. 4A-4B, in accordance with embodiments of the disclosure.

FIG. 7 is a perspective view of a nasal droplet delivery device of FIG. 4A-4B without the drug delivery ampoule inserted, in accordance with embodiments of the disclosure.

FIGS. 8A-8B are perspective views of a drug delivery ampoule and nosepiece cover, showing a front view (FIG. 8A) and back view (FIG. 8B), in accordance with embodiments of the disclosure.

FIGS. 9A-9C show an alternative drug delivery ampoule, with FIG. 9A showing a perspective view, FIG. 9B showing a top exploded view, and FIG. 9C showing a bottom exploded view.

FIG. 10 is a perspective view of a drug delivery ampoule with a nosepiece attached, in accordance with an embodiment of the disclosure.

FIGS. 11A-11B show front (FIG. 11A) and back (FIG. 11B) views of an exemplary nosepiece, in accordance with an embodiment of the disclosure.

FIG. 12 is a back perspective view of an exemplary nosepiece including an air intake flow element, in accordance with an embodiment of the disclosure.

DETAILED DESCRIPTION

In certain aspects of the disclosure, a nasal droplet delivery device, or nasal soft mist inhaler (SMI) device (these terms are used interchangeably herein) is disclosed. The nasal SMI is a novel nasal drug delivery device that overcomes limitations of the currently available nasal drug delivery devices.

In certain aspects, the present disclosure generally relates to a nasal droplet delivery device and method of delivering safe, suitable, and repeatable dosages of ejected droplets to a subject for nasal drug delivery. The nasal droplet delivery device and method is capable of delivering a defined volume of fluid in the form of ejected droplets having properties that deliver an adequate and repeatable high percentage ejection for delivery via the nasal passageways and sinus cavities.

The present disclosure provides a nasal droplet delivery device for delivery of a fluid as an ejected stream of droplets to the nasal passageways and sinus cavities of a subject, the device comprising a housing, a nosepiece, a reservoir for receiving a volume of fluid, and an ejector mechanism including a piezoelectric actuator and an aperture plate, wherein the ejector mechanism is configured to eject a stream of droplets. In some embodiments, the ejected stream of droplets have an average ejected droplet diameter within a range to deposit at least 50% of the ejected droplets into the nasal passageways and sinus cavities, and to minimize passage of droplets to the pulmonary system during use. In some embodiments, the ejected stream of droplets have an average ejected droplet diameter of greater than about 6 microns, preferably greater than about 10 microns.

As shown in further detail herein, the nasal droplet delivery device is configured in an in-line orientation in that the housing, its internal components, and various device components (e.g., the nosepiece, air inlet flow element, etc.) are orientated in a substantially in-line or parallel configuration (e.g., along the airflow path) so as to form a small, hand-held device. In certain embodiments, the housing and ejector mechanism are oriented such that the exit side of aperture plate is perpendicular to the direction of airflow and the stream of droplets is ejected in parallel to the direction of airflow. In other embodiments, the housing and ejector mechanism are oriented such that the exit side of aperture plate is parallel to the direction of airflow and the stream of droplets is ejected substantially perpendicularly to the direction of airflow such that the ejected stream of droplets is directed through the housing at an approximate 90 degree change of trajectory prior to expulsion from the housing.

In specific embodiments, the ejector mechanism is electronically breath activated by at least one differential pressure sensor located within the housing of the nasal droplet delivery device upon sensing a pre-determined pressure change within the nosepiece. In certain embodiments, such a pre-determined pressure change may be sensed during an inhalation cycle by a user of the device, as will be explained in further detail herein.

In some aspects, the nasal droplet delivery device further includes an air inlet flow element positioned in the airflow at the airflow entrance of the housing and configured to facilitate non-turbulent (i.e., laminar and/or transitional) airflow across the exit side of aperture plate and to provide sufficient airflow to ensure that the ejected stream of droplets flows through the droplet delivery device during use. In some embodiments, the air inlet flow element may be positioned within the nosepiece.

As will be described in further detail herein, the air inlet flow element may be positioned behind the exit side of the aperture plate along the direction of airflow, or in-line or in front of the exit side of the aperture plate along the direction of airflow. In certain embodiments, the air inlet flow element comprises one or more openings formed there through and configured to increase or decrease internal pressure resistance within the nasal droplet delivery device during use. For instance, the air inlet flow element may comprise an array of one or openings. In certain embodiments, the air inlet flow element may comprise one or more interior baffles or substantially cylinder air flow elements, e.g., wherein the one or more interior baffles or cylinders comprise one or more airflow openings.

In one aspect, the present disclosure includes and provides a nasal droplet delivery device for delivering an ejected stream of droplets via the nasal passageways and sinus cavities of a subject, the device including a housing, a reservoir (drug chamber) for receiving a volume of fluid, an ejector mechanism in fluid communication with the reservoir and configured to eject a stream of droplets having an average ejected droplet diameter within a range to deposit at least 50% of the ejected droplets into the nasal passageways and sinus cavities, and to minimize passage of droplets to the pulmonary system during use.

In certain embodiments, the nasal droplet delivery device may include: a housing; a nosepiece positioned at the airflow exit side of the housing; a reservoir disposed within or in fluid communication with the housing for receiving a volume of fluid; an ejector mechanism in fluid communication with the reservoir, the ejector mechanism comprising a piezoelectric actuator and an aperture plate, the aperture plate having a plurality of openings formed through its thickness and the piezoelectric actuator operable to oscillate the aperture plate at a frequency to thereby generate an ejected stream of droplets, at least one differential pressure sensor positioned within the housing; the at least one differential pressure sensor configured to activate the ejector mechanism upon sensing a pre-determined pressure change within the nosepiece to thereby generate an ejected stream of droplets; the ejector mechanism configured to generate the ejected stream of droplets wherein at least about 50% of the droplets are deposited into the nasal passageways and sinus cavities during use. In some embodiments, the ejector mechanism is configured to generate the ejected stream of droplets wherein at least about 50% of the droplets have an average ejected droplet diameter of greater than about 6 microns, e.g., between about 10 microns and about 100 microns, such that at least about 50% of the mass of the ejected stream of droplets is delivered into the nasal passageways and sinus cavities of a subject during use.

In accordance with certain aspects of the disclosure, aerosol droplets are sized to have a sufficiently small size so as to have a low inertial force and low momentum such that they are transported almost completely by motion of an air stream, (entrained air), into the nasal passageways and sinus cavities, but yet have a sufficiently large size so as to minimize passage through the naso-pharynx into the pulmonary system during use. By way of example, the aerosol droplets may have an average droplet size (mass mean aerodynamic diameter, MMAD) of greater than about 6 microns, greater than about 10 microns, between about 6 and about 300 microns, between about 10 and about 300 microns, between about 6 and about 100 microns, between about 6 and about 100 microns, between about 10 and about 100 microns, between about 10 and about 80 microns, between about 6 and about 80 microns, between about 10 and about 50 microns, between about 6 and about 50 microns, between about 10 and about 40 microns, between about 6 and about 40 microns, between about 10 and about 30 microns, between about 6 and about 30 microns, between about 10 and about 20 microns, between about 6 and about 20 microns, between about 10 and about 18 microns, between about 6 and about 18 microns, between about 10 and about 15 microns, between about 6 and about 15 microns, between about 10 and about 13 microns, between about 6 and about 13 microns, between about 14 and about 18 microns, etc.

In certain aspects, the present disclosure provides methods and devices for delivering an aerosol via the nasal passageways and sinus cavities for the delivery of small molecule, large molecule and biologic medicaments for local or systemic drug delivery. The methods and devices of the disclosure are specifically configured to provide aerosol droplet sizes sufficiently small size so as to have a low inertial force and low momentum such that they are transported almost completely by motion of an air stream, (entrained air), into the nasal passageways and sinus cavities, but yet have a sufficiently large size so as to minimize passage through the naso-pharynx into the pulmonary system during use, such that effective, repeatable dose delivery is achieved. Further, the methods of the devices of the disclosure generate aerosols in a manner that does not generate elevated in-situ temperatures or forces that may tend to denature or decompose active agents. As such, the methods and devices of the disclosure may be used to deliver biologics and other large molecules that might otherwise be susceptible to denaturing and degradation.

The present disclosure includes and provides an ejector mechanism constructed to eject an aerosol stream of droplets. The ejector mechanism and ejector systems are comprised of an aperture plate that is coupled to a piezoelectric actuator. In certain implementations, the aperture plate may be coupled to an actuator plate that is coupled to the piezoelectric actuator. The aperture plate contains a plurality of openings formed through its thickness and the piezoelectric actuator oscillates the aperture plate, having fluid in contact with one surface of the aperture plate, at a frequency and voltage to generate a directed aerosol stream of droplets through the smaller openings of the aperture plate via the nasal passageways and sinus cavities, as the patient inhales. In other implementations where the aperture plate is coupled to the actuator plate, the actuator plate is oscillated by the piezoelectric oscillator at a frequency and voltage to generate a directed aerosol stream or plume of aerosol droplets.

The present disclosure includes and provides a nasal drug delivery apparatus (i.e. device) that can utilize a drug containing cartridge and/or cartridge/ejector assembly, (a combined drug/ejector module unit), that can be replaced/disposed either on a daily or weekly or monthly basis suitable to the prescribed treatment. In certain aspects this system and method provides a disposable/replaceable, drug/ejector module unit that may minimize and prevent buildup of surface deposits or surface microbial contamination on the aperture plate, owing to its short in-use time.

The present disclosure also includes and provides a disposable/removable drug cartridge/ejector module unit that is horizontally oriented and positioned such that the fluid or drugs contained therein are in constant contact with the entrance surface of the aperture plate. The horizontally oriented drug/ejector module allows and provides a uniform distribution of fluid and a uniform coating of fluid onto the aperture plate. In some implementations the horizontally positioned drug/ejector module provides an aperture plate with a uniform fluid/drug coating that also has the benefit of providing a uniform load across the aperture plate. This design provides a more efficient and stable aperture plate oscillation and may provide for a more efficient ejection of fluid and minimizes the probability of chaotic membrane oscillations. In certain aspects, chaotic oscillations may lead to delivery of improper dosages as well as minimize or stop ejection altogether or lead to deposition of fluid and/or drug onto the aperture plate surfaces and lead to blockage of apertures. The reduction or elimination of chaotic oscillations provide a more efficient and stable aperture plate oscillation and a more efficient and stable delivery of medication.

The present disclosure provides a droplet delivery device for delivery of a fluid as an ejected stream of droplets via the nasal passageways and sinus cavities of a subject, the device comprising a housing, a reservoir for receiving a volume of fluid, and an ejector mechanism including a piezoelectric actuator and an aperture plate, wherein the ejector mechanism is configured to eject a stream of droplets having an average ejected droplet diameter greater than about 6 microns, preferably greater than about 10 microns, e.g., between about 10 microns and about 100 microns. As shown in further detail herein, the droplet delivery device is configured in an in-line orientation in that the housing, ejector mechanism and related electronic components are orientated in a generally in-line or parallel configuration so as to form a small, hand-held device.

In specific embodiments, the ejector mechanism is electronically breath activated by at least one differential pressure sensor located within the housing of the droplet delivery device upon sensing a pre-determined pressure change within the housing. In certain embodiments, such a pre-determined pressure change may be sensed during a nasal inhalation by a user of the device, as will be explained in further detail herein.

In accordance with certain aspects of the disclosure a key parameter in defining the efficiency of nasal aerosol delivery systems is the particle size distribution of the aerosol cloud, as this is a predictor of the deposition site for the drug within the nasal passages. To increase nasal deposition and minimize deposition in the lungs and gastro-intestinal tract, aerosol droplets should generally have a mass median aerodynamic diameter greater than 10 to 20 microns. Below this range reduced naso-pharyngeal deposition and increased pulmonary deposition occurs. Without intending to be limited by theory, effective delivery to the nasal passages and sinus cavities requires that a droplet delivery device must impart a momentum that is sufficiently high to permit ejection out of the device while providing droplets of sufficient diameter to avoid naso-pharyngeal and pulmonary deposition.

In certain aspects, the present disclosure includes and provides an ejector mechanism configured to eject a stream of droplets within the respirable range of greater than about 6 microns, preferably greater than about 10 microns, etc. The ejector mechanism is comprised of an aperture plate that is directly or indirectly coupled to a piezoelectric actuator. In certain implementations, the aperture plate may be coupled to an actuator plate that is coupled to the piezoelectric actuator. The aperture plate generally includes a plurality of openings formed through its thickness and the piezoelectric actuator directly or indirectly (e.g. via an actuator plate) oscillates the aperture plate, having fluid in contact with one surface of the aperture plate, at a frequency and voltage to generate a directed aerosol stream of droplets through the openings of the aperture plate into the nasal passageways and sinus cavities, as the patient inhales. In other implementations where the aperture plate is coupled to the actuator plate, the actuator plate is oscillated by the piezoelectric oscillator at a frequency and voltage to generate a directed aerosol stream or plume of aerosol droplets.

In certain aspects, the present disclosure relates to a droplet delivery device for delivering a fluid as an ejected stream of droplets via the nasal passageways and sinus cavities of a subject. In certain aspects, the therapeutic agents may be delivered at a high dose concentration and efficacy, as compared to alternative dosing routes and standard nasal aerosol technologies.

In certain embodiments, the droplet delivery devices of the disclosure may be used to treat various diseases, disorders and conditions by delivering therapeutic agents via the nasal passageways and sinus cavities of a subject. In this regard, the droplet delivery devices may be used to deliver therapeutic agents both locally (e.g., for nasal or sinus disease, conditions and disorders) and systemically to the body.

More specifically, the droplet delivery device may be used for the local delivery of therapeutic agents to the nasal passageway and sinus cavities of a subject. For instance, therapeutic agents such as the following may be delivered using the droplet delivery device of the disclosure:

| Generic Name | Brand Name | Class | Use |
| --- | --- | --- | --- |
| Azelastine | Astelin Nasal Spray | Antihistamine | Management of symptoms associated with seasonal allergic rhinitis (hay fever) in children and adults over 5 years of age. Management of symptoms associated with non-allergic/vasomotor rhinitis and allergic rhinitis (hay fever) ages 12 and above. |
| | Astepro (0.1%, 0.15%) | Antihistamine | Seasonal and perennial allergic rhinitis (hay fever) age 12 and older. |
| Azelastine and Fluticasone Propionate | Dymista | Nasal Antihistamine and Nasal Steroid | Seasonal allergic rhinitis (hay fever) ages 12 and over |
| Beclomethasone Diprorionate (Dry nasal spray) | Q-Nasl | Steroid | Seasonal and perennial nasal allergies (hay fever) in 12 years or older |
| Budesonide | Rhinocort | Nasal Steroids | Seasonal and year round allergic rhinitis (hay fever) age 6 and older. |
| Ciclesonide | Omnaris Nasal Spray | Nasal Steroids | Management of nasal symptoms associated with: Seasonal allergic rhinitis (hay fever) age 6 and older. Year round or perennial allergic rhinitis (hay fever) age 12 and older. |
| | Zetonna | Steroid | Seasonal and perennial nasal allergies (hay fever) in 12 years or older |
| Cromolyn Sodium | Nasalcrom Nasal Spray | Mast Cell Inhibitor | To prevent and relieve symptoms of allergic rhinitis (hay fever). |
| Flunisolide | Generic: Flunisolide 0.025% Solution | Nasal Steroids | Seasonal and year round allergic rhinitis (hay fever) age 6 and older. |
| Fluticasone Furoate | Veramyst Nasal Spray | | Management of symptoms associated with seasonal and perennial allergic rhinitis (hay fever) age 2 and older. |
| | Flonase Sensimist | | Seasonal and perennial allergic rhinitis (hay fever) |
| Fluticasone Propionate | Flonase Nasal Spray Fluticasone Nasal Propionate Generic | | Management of nasal symptoms associated with seasonal and year-round allergic and non-allergic rhinitis (hay fever). |
| Ipratropium Bromide | Atrovent Nasal Spray 0.03% Ipratropium Nasal Spray; 0.06% | Anticholinergic | 0.03%; Management of symptoms associated with rhinorrhea (runny nose) that is associated with seasonal allergic (hay fever) and non-allergic or vasomotor rhinitis. For children 6 and older and adults. 0.06%; Above age 5; Symptoms such as runny nose associated with allergies and colds. |
| Mometasone Furoate Monohydrate | Nasonex Nasal Spray | | Management of symptoms of allergic rhinitis (hay fever) (seasonal and year-round) age 2 and older. Prevention of seasonal allergic rhinitis (hay fever) symptoms age 12 and older (starting a 2 to 4 weeks before the season begins). |

-continued

| Generic Name | Brand Name | Class | Use |
| --- | --- | --- | --- |
| Olopatadine | Patanase | Antihistamine | Management of symptoms associated with seasonal allergic rhinitis (hay fever) age 12 and older. |
| Oxymetazoline | Afrin and many other brands. | Decongestant | To reduce nasal swelling. |
| Triamcinolone Acetonide | Nasacort AQ | | Management of symptoms associated with seasonal and perennial allergic rhinitis (hay fever) age 6 and older. |

In other embodiments, the droplet delivery device may be used for the systemic delivery of therapeutic agents including small molecules, therapeutic peptides, proteins, antibodies, and other bioengineered molecules via the nasal passageways and sinus cavities of a subject. By way of non-limiting example, the droplet delivery device may be used to systemically deliver therapeutic agents for the treatment or prevention of indications inducing, e.g., migraine, diabetes mellitus, rheumatoid arthritis, plaque psoriasis, Crohn's disease, hormone replacement, neutropenia, nausea, influenza, pain management, opioid overdose, etc.

By way of non-limiting example, therapeutic peptides, proteins, antibodies, and other bioengineered molecules include: growth factors, insulin, vaccines (Prevnor—Pneumonia, Gardasil—HPV), antibodies (Keytruda (pembrolizumab), Opdivo (nivolumab) Avastin (bevacizumab), Humira (adalimumab), Remicade (infliximab), Herceptin (trastuzumab)), Fc Fusion Proteins (Enbrel (etanercept), Orencia (abatacept)), hormones (Elonva-long acting FSH, Growth Hormone), enzymes (Pulmozyme—rHu-DNAase-), other proteins (Clotting factors, Interleukins, Albumin), gene therapy and RNAi, cell therapy (Provenge—Prostate cancer vaccine), antibody drug conjugates—Adcetris (Brentuximab vedotin for HL), cytokines, anti-infective agents, polynucleotides, oligonucleotides (e.g., gene vectors), or any combination thereof; or solid droplets or suspensions such as Flonase (fluticasone propionate) or Advair (fluticasone propionate and salmeterol xinafoate).

By way of non-limiting example, small molecule drugs, therapeutic peptides, proteins, antibodies, and other bioengineered molecules include: pain management treatments and opioids (fentanyl, morphine, etc.), opioid overdose treatments (naloxone, etc.) triptan and migraine treatments (sumatriptan, zolmitriptan, rizatriptan, dihydroergotamine), growth factors, insulin, vaccines (Prevnor—Pneumonia, Gardasil—HPV), antibodies (Keytruda (pembrolizumab), Opdivo (nivolumab) Avastin (bevacizumab), Humira (adalimumab), Remicade (infliximab), Herceptin (trastuzumab)), Fc Fusion Proteins (Enbrel (etanercept), Orencia (abatacept)), hormones (Elonva-long acting FSH, Growth Hormone), enzymes (Pulmozyme—rHu-DNAase-), other proteins (Clotting factors, Interleukins, Albumin), gene therapy and RNAi, cell therapy (Provenge—Prostate cancer vaccine), antibody drug conjugates—Adcetris (Brentuximab vedotin for HL), cytokines, anti-infective agents, polynucleotides, oligonucleotides (e.g., gene vectors), or any combination thereof; or solid droplets or suspensions such as Flonase (fluticasone propionate) or Advair (fluticasone propionate and salmeterol xinafoate).

In other aspects of the disclosure, methods for generating an ejected stream of droplets for delivery via the nasal passageways and sinus cavities of a subject using the droplet delivery devices of the disclosure are provided. In certain embodiments, the ejected stream of droplets is generated in a controllable and defined droplet size range. By way of example, the droplet size range includes at least about 50%, at least about 60%, at least about 70%, at least about 85%, at least about 90%, between about 50% and about 90%, between about 60% and about 90%, between about 70% and about 90%, etc., of the ejected droplets are greater than 6 microns, greater than 10 microns, between 10 and 300 microns, between 10 and 100 microns, between 10 and 80 microns, between 10 and 50 microns, between 10 and 30 microns, etc.

In other embodiments, the ejected stream of droplets may have one or more diameters, such that droplets having multiple diameters are generated so as to target multiple regions of the nasal passageway and/or sinus cavities.

In another embodiment, methods for delivering safe, suitable, and repeatable dosages of a medicament to the pulmonary system using the droplet delivery devices of the disclosure are provided. The methods deliver an ejected stream of droplets to the desired location within the pulmonary system of the subject, including the deep lungs and alveolar airways.

In certain aspects of the disclosure, a nasal droplet delivery device for delivery an ejected stream of droplets to the pulmonary system of a subject is provided. The nasal droplet delivery device generally includes a housing, a nosepiece positioned at the airflow exit side of the housing, a reservoir disposed in or in fluid communication with the housing for receiving a volume of fluid, an ejector mechanism in fluid communication with the reservoir, and at least one differential pressure sensor positioned within the housing. The housing, its internal components, and various device components (e.g., the nosepiece, air inlet flow element, etc.) are orientated in a substantially in-line or parallel configuration (e.g., along the airflow path) so as to form a small, hand-held device. The differential pressure sensor is configured to electronically breath activate the ejector mechanism upon sensing a pre-determined pressure change within the nosepiece, and the ejector mechanism is configured to generate an ejected stream of droplets.

In certain embodiments, the nosepiece may be interfaced with (and optionally removable and/or replaceable), integrated into, or part of the housing. In other embodiments, the nosepiece may be interfaced with (and optionally removable and/or replaceable), integrated into, or part of the drug delivery ampoule.

The ejector mechanism may include a piezoelectric actuator which is directly or indirectly coupled to an aperture plate having a plurality of openings formed through its thickness. The piezoelectric actuator is operable to directly or indirectly oscillate the aperture plate at a frequency to thereby generate an ejected stream of droplets.

In certain embodiments, the housing and ejector mechanism are oriented such that the exit side of aperture plate is perpendicular to the direction of airflow and the stream of droplets is ejected in parallel to the direction of airflow. In other embodiments, the housing and ejector mechanism are oriented such that the exit side of aperture plate is parallel to the direction of airflow and the stream of droplets is ejected substantially perpendicularly to the direction of airflow such that the ejected stream of droplets is directed through the housing at an approximate 90 degree change of trajectory prior to expulsion from the housing.

In certain embodiments, the nasal droplet delivery device is comprised of a separate drug delivery ampoule with an ejector mechanism (e.g., combination reservoir/ejector mechanism module) embedded within a surface of a drug reservoir, and a handheld base unit (e.g., housing) including a differential pressure sensor, a microprocessor and three AAA batteries. In certain embodiments, the handheld base unit also includes a nosepiece, optionally removable, an optional nosepiece cover, and an optional ejector plate seal. The microprocessor controls dose delivery, dose counting and software designed monitoring parameters that can be transmitted through blue-tooth technology. The ejector mechanism optimizes droplet delivery to the lungs by creating an ejected droplet stream in a predefined range with a high degree of accuracy and repeatability.

In certain embodiments, the nasal droplet delivery device may include a combination reservoir/ejector mechanism module (e.g., drug delivery ampoule) that may be replaceable or disposable either on a periodic basis, e.g., a daily, weekly, monthly, as-needed, etc. basis, as may be suitable for a prescription or over-the-counter medication. The reservoir may be prefilled and stored in a pharmacy for dispensing to patients or filled at the pharmacy or elsewhere by using a suitable injection means such as a hollow injection syringe driven manually or driven by a micro-pump. The syringe may fill the reservoir by pumping fluid into or out of a rigid container or other collapsible or non-collapsible reservoir. In certain aspects, such disposable/replaceable, combination reservoir/ejector mechanism module may minimize and prevent buildup of surface deposits or surface microbial contamination on the aperture plate, owing to its short in-use time.

In certain aspects of the disclosure, the ejector mechanism, reservoir, and housing/nosepiece function to generate a plume with droplet diameters greater than about 6 μm, preferably greater than about 10 μm. As discussed above, in certain embodiments, the reservoir and ejector mechanism modules are powered by electronics in the device housing and a reservoir which may carry sufficient drug for a single dose, just a few doses, or several hundred doses of medicament.

The present disclosure also provides a nasal droplet delivery device that is altitude insensitive. In certain implementations, the nasal droplet delivery device is configured so as to be insensitive to pressure differentials that may occur when the user travels from sea level to sub-sea levels and at high altitudes, e.g., while traveling in an airplane where pressure differentials may be as great as 4 psi. As will be discussed in further detail herein, in certain implementations of the disclosure, the nasal droplet delivery device may include a superhydrophobic filter, optionally in combination with a spiral vapor barrier, which provides for free exchange of air into and out of the reservoir, while blocking moisture or fluids from passing into the reservoir, thereby reducing or preventing fluid leakage or deposition on aperture plate surfaces.

In certain aspects, the devices of the disclosure eliminate the need for patient/device coordination by using a differential pressure sensor to initiate the piezoelectric ejector in response to the onset of inhalation. The device does not require manual triggering of medication delivery. Unlike propellant driven MDIs, the droplets from the devices of the disclosure are generated having little to no intrinsic velocity from the aerosol formation process and are inhaled into the nasal passageway solely by the user's incoming breath passing through the nosepiece. The droplets will ride on entrained air providing improved deposition into the target site.

In certain embodiments, as described in further detail herein, when the drug ampoule is mated to the handheld base unit, electrical contact is made between the base containing the batteries and the ejector mechanism embedded in the drug reservoir. In certain embodiments, visual indications, e.g., a horizontal series of three user visible LED lights, and audio indications via a small speaker within the handheld base unit may provide user notifications. By way of example, the device may be, e.g., 2.0-3.5 cm high, 5-7 cm wide, 10.5-12 cm long and may weight approximately 95 grams with an empty drug ampoule and with batteries inserted.

As described herein, in certain embodiments, the nasal droplet delivery device may be turned on and activated for use by inserting the drug ampoule into the base unit, opening the nosepiece cover, and/or switching an on/off switch/slide bar. In certain embodiments, visual and/or audio indicators may be used to indicate the status of the device in this regard, e.g., on, off, stand-by, preparing, etc. By way of example, one or more LED lights may turn green and/or flash green to indicate the device is ready for use. In other embodiments, visual and/or audio indicators may be used to indicate the status of the drug ampoule, including the number of doses taken, the number of doses remaining, instructions for use, etc. For example, and LED visual screen may indicate a dose counter numerical display with the number of remaining doses in the reservoir.

As described in further detail herein, during use as a user inhales through the nosepiece of the housing of a nasal droplet delivery device of the disclosure, a differential pressure sensor within the housing detects inspiratory flow, e.g., by measuring the pressure drop across a Venturi plate at the back of the nosepiece. When a threshold pressure decline (e.g., 8-15 slm) is attained, the microprocessor activates the ejector mechanism, which in turn generates an ejected stream of droplets into the airflow of the device that the user inhales through the nosepiece. In certain embodiments, audio and/or visual indicates may be used to indicate that dosing has been initiated, e.g., one or more LEDs may illuminate green. The microprocessor then deactivates the ejector at a designated time after initiation so as to achieve a desired administration dosage, e.g., 1-1.45 seconds. In certain embodiments, as described in further detail herein, the device may provide visual and/or audio indicators to facilitate proper dosing, e.g., the device may emit a positive chime sound after the initiation of dosing, indicating to the user to begin holding their breath for a designated period of time, e.g., 3-10 seconds. During the breath hold period, e.g., the three green LEDs may blink. Additionally, there may be voice commands instructing the patient on proper times to exhale, inhale and hold their breath, with an audio indicator of a breath hold countdown.

Following dosing, the nasal droplet delivery device may turned off and deactivated in any suitable manner, e.g., by closing the nosepiece cover, switching an on/off switch/slide bar, timing out from non-use, removing the drug ampoule, etc. If desired, audio and/or visual indicators may prompt a user to deactivate the device, e.g., by flashing one or more red LED lights, providing voice commands to close the nosepiece cover, etc.

In certain embodiments, the nasal droplet delivery device may include an ejector mechanism closure system that seals the aperture plate when not in use to protect the integrity of the aperture plate and to minimize and prevent contamination and evaporation of the fluid within the reservoir. For example, in some embodiments, the device may include a nosepiece cover that comprises a rubber plug that is sized and shaped to seal the exit side surface of the aperture plate when the cover is closed. In other embodiments, the nosepiece cover may trigger a slide to seal the exit side surface of the aperture plate when the cover is closed. Other embodiments and configurations are also envisioned, e.g., manual slides, covers, and plugs, etc. In certain aspects, the microprocessor may be configured to detect when the ejector mechanism closure, aperture plate seal, etc. is in place, and may thereafter deactivate the device.

Several features of the device allow precise dosing of specific droplet sizes. Droplet size is set by the diameter of the holes in the mesh which are formed with high accuracy. By way of example, the holes in the aperture plate may range in size from 1 μm to 100 μm, from 2 μm to 50 μm, from 3 μm to 40 μm, from 4 μm to 40 μm, etc. Ejection rate, in droplets per second, is generally fixed by the frequency of the aperture plate vibration, e.g., 108-kHz, which is actuated by the microprocessor. In certain embodiments, there is less than a 50-millisecond lag between the detection of the start of inhalation and full droplet generation.

Other aspects of the device of the disclosure that allow for precise dosing of specific droplet sizes include the production of droplets within the desired range early in the inhalation cycle, thereby minimizing the amount of drug product being deposited in the nasal passageway and sinus cavity at the end of an inhalation. In addition, the design of the drug ampoule allows the aperture plate surface to be wetted and ready for ejection without user intervention, thus obviating the need for shaking and priming. Further, the design of the drug ampoule vent configuration together with the ejector mechanism closure system limits fluid evaporation from the reservoir to less than 150 μL to 350 μL per month.

The device may be constructed with materials currently used in FDA cleared devices. Standard manufacturing methods may be employed to minimize extractables.

Any suitable material may be used to form the housing of the droplet delivery device. In particular embodiment, the material should be selected such that it does not interact with the components of the device or the fluid to be ejected (e.g., drug or medicament components). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc.

The drug ampoule may be constructed of any suitable materials for the intended pharmaceutical use. In particular, the drug contacting portions may be made from material compatible with the desired active agent(s). By way of example, in certain embodiments, the drug only contacts the inner side of the drug reservoir and the inner face of the aperture plate and piezoelectric element. Wires connecting the piezoelectric ejector mechanism to the batteries contained in the base unit may be embedded in the drug ampoule shell to avoid contact with the drug. The piezoelectric ejector may be attached to the drug reservoir by a flexible bushing. To the extent the bushing may contact the drug fluid, it may be, e.g., any suitable material known in the art for such purposes such as those used in piezoelectric nebulizers.

In certain embodiments, the device nosepiece may be removable, replaceable and may be cleaned. Similarly, the device housing and drug ampoule can be cleaned by wiping with a moist cloth. In certain embodiments, the nosepiece may be interfaced with (and optionally removable and/or replaceable), integrated into, or part of the housing. In other embodiments, the nosepiece may be interfaced with (and optionally removable and/or replaceable), integrated into, or part of the drug delivery ampoule.

Again, any suitable material may be used to form the nosepiece of the nasal droplet delivery device. In particular embodiment, the material should be selected such that it does not negatively interact with the components of the device or the fluid to be ejected (e.g., drug or medicament components). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc. In certain embodiments, the nosepiece may be removable, replaceable and sterilizable. This feature improves sanitation for drug delivery by providing a mechanism to minimize buildup of aerosolized medication within the nosepiece and by providing for ease of replacement, disinfection and washing. In one embodiment, the nosepiece tube may be formed from sterilizable and transparent polymer compositions such as polycarbonate, polyethylene or polypropylene, as discussed herein.

In certain aspects of the disclosure, an electrostatic coating may be applied to the one or more portions of the housing, e.g., inner surfaces of the housing along the airflow pathway such as the nosepiece, to aid in reducing deposition of ejected droplets during use due to electrostatic charge build-up. Alternatively, one or more portions of the housing may be formed from a charge-dissipative polymer. For instance, conductive fillers are commercially available and may be compounded into the more common polymers used in medical applications, for example, PEEK, polycarbonate, polyolefins (polypropylene or polyethylene), or styrenes such as polystyrene or acrylic-butadiene-styrene (ABS) copolymers. Alternatively, in certain embodiments, one or more portions of the housing, e.g., inner surfaces of the housing along the airflow pathway such as the nosepiece, may be coated with anti-microbial coatings, or may be coated with hydrophobic coatings to aid in reducing deposition of ejected droplets during use. Any suitable coatings known for such purposes may be used, e.g., polytetrafluoroethylene (Teflon).

In yet other aspects, the aperture plate of the droplet delivery device comprises a domed shape. The aperture plate may be composed of either pure metal, metal alloy or high modulus polymeric materials, such as, and not limited by example, Ni, NiCo, Pd, Pt, NiPd, or other metals or alloy combinations. For instance, the aperture plate may be formed of any suitable material including a metal, e.g., stainless steel, nickel, cobalt, titanium, iridium, platinum, or palladium or alloys thereof. Alternatively, the aperture plate can be formed of suitable material, including other metals or polymers. In certain embodiments, the aperture plate is comprised of, e.g., poly ether ether ketone (PEEK), polyimide, polyetherimide, polyvinylidine fluoride (PVDF), ultra-high molecular weight polyethylene (UHMWPE), nickel, nickel-cobalt, palladium, nickel-palladium, platinum, or other suitable metal alloys, and combinations thereof.

A preferred high modulus polymeric material for fabrication of an aperture plate is polyether ether ketone (PEEK). However a number of high modulus polymeric materials such as polyimide (Kapton), polyetherimide (Ultem), polyvinylidine fluoride (PVDF), and ultra-high molecular weight polyethylene (UHMWPE), as well as a range of filler materials blended into polymers to enhance physical and chemical properties may be used for aperture plate designs and fabrication. Filler materials can include but are not limited to glass and carbon nanotubes. These materials may be used to increase the yield strength and the stiffness or modulus of elasticity.

Another implementation of the disclosure provides an aperture plate which contain fluted holes or nozzles that cover the entire area of the aperture plate and a dome shape located at the center of the mesh. The active area of the dome is located at the top of the dome. The active area is defined as the area from which droplets are ejected from the fluted holes or nozzles contained therein during actuation.

Any suitable differential pressure sensor with adequate sensitivity to measure pressure changes obtained during standard inhalation cycles may be used, e.g., ±5 SLM, 10 SLM, 20 SLM, etc. For instance, pressure sensors from Sensirion, Inc., SDP31 or SDP32 (U.S. Pat. No. 7,490,511 B2) are particularly well suited for these applications.

In certain aspects, the microprocessor in the device may be programmed to ensure exact timing and actuation of the ejector mechanism in accordance with desired parameters, e.g., based duration of piezoelectric activation to achieve desired dosages, etc. In certain embodiments, the device includes or interfaces with a memory (on the device, smartphone, App, computer, etc.) to record the date-time of each ejection event, as well as the user's inhalation flow rate during the dose inhalation to facilitate user monitoring, as well as drug ampoule usage monitoring. For instance, the microprocessor and memory can monitor doses administered and doses remaining in a particular drug ampoule. In certain embodiments, the drug ampoule may comprise components that include identifiable information, and the base unit may comprise components that may "read" the identifiable information to sense when a drug ampoule has been inserted into the base unit, e.g., based on a unique electrical resistance of each individual ampoule, an RFID chip, or other readable microchip (e.g., cryptoauthentication microchip). Dose counting and lockouts may also be preprogramed into the microprocessor.

In certain embodiments of the present disclosure, the signal generated by the pressure sensors provides a trigger for activation and actuation of the ejector mechanism to thereby generate droplets and delivery droplets at or during a peak period of a patient's inhalation (inspiratory) cycle and assures optimum deposition of the plume of droplets and delivery of the medication into the nasal passageway or sinus cavity of the user.

In accordance with certain aspects of the disclosure, the nasal droplet delivery device provides a reliable monitoring system that can date and time stamp actual deliver of medication, e.g., to benefit patients through self-monitoring or through involvement of care givers and family members.

As described in further detail herein, the nasal droplet delivery device of the disclosure may detect inhalation airflow through the nasal passageway and record/store inspiratory airflow in a memory (on the device, smartphone, App, computer, etc.). A preset threshold (e.g., 8-10 slm) triggers delivery of medication over a defined period of time, e.g., 1-1.5 seconds. Inspiratory flow is sampled frequently until flow stops. The number of times that delivery is triggered is incorporated and displayed in the dose counter LED on the device. Blue tooth capabilities permit the wireless transmission of the data.

Bluetooth communication in the device will communicate date, time and number of actuations per session to the user's smartphone. Software programing can provide charts, graphics, medication reminders and warnings to patients and whoever is granted permission to the data. The software application will be able to incorporate multiple medications that use the device of the disclosure (e.g. pain control medication, inhaled steroid, etc.).

The device of the disclosure can also provide directed instruction to users, including audio and visual indicators to facilitate proper use of the device and proper dosing. The device of the present disclosure is configured to dispense droplets during the correct part of the inhalation cycle, and can including instruction and/or coaching features to assist patients with proper device use, e.g., by instructing the holding of breath for the correct amount of time after inhalation. The device of the disclosure allows this dual functionality because it may both monitor air flow during the inhalation, and has internal sensors/controls which may detect the end of inhalation (based upon measured flow rate) and can cue the patient to hold their breath for a fixed duration after the inhalation ceases.

In one exemplary embodiment, a patient may be coached to hold their breath with an LED that is turned on at the end of inhalation and turned off after a defined period of time (i.e., desired time period of breath hold), e.g., 10 seconds. Alternatively, the LED may blink after inhalation, and continue blinking until the breath holding period has ended. In this case, the processing in the device detects the end of inhalation, turns on the LED (or causes blinking of the LED, etc.), waits the defined period of time, and then turns off the LED. Similarly, the device can emit audio indications, e.g., one or more bursts of sound (e.g., a 50 millisecond pulse of 1000 Hz), verbal instructions to hold breath, verbal countdown, music, tune, melody, etc., at the end of inhalation to cue a patient to hold their breath for the during of the sound signals. If desired, the device may also vibrate during or upon conclusion of the breath holding period.

In certain embodiments, the device provides a combination of audio and visual methods (or sound, light and vibration) described above to communicate to the user when the breath holding period has begun and when it has ended. Or during the breath holding to show progress (e.g., a visual or audio countdown).

In other aspects, the device of the disclosure may provide coaching to inhale longer, more deeply, etc. The average peak inspiratory flow during inhalation (or dosing) can be utilized to provide coaching. For example, a patient may hear a breath deeper command until they reach 90% of their average peak inspiratory flow as measured during inspiration (dosing) as stored on the device, phone or in the cloud.

In addition, an image capture device, including cameras, scanners, or other sensors without limitation, e.g. charge coupled device (CCD), may be provided to detect and measure the ejected aerosol plume. These detectors, LED, delta P transducer, CCD device, all provide controlling signals to a microprocessor or controller in the device used for monitoring, sensing, measuring and controlling the ejection of a plume of droplets and reporting patient compliance, treatment times, dosage, and patient usage history, etc., via Bluetooth, for example.

Reference will now be made to the figures, with like components illustrates with like references numbers.

Figure 5:
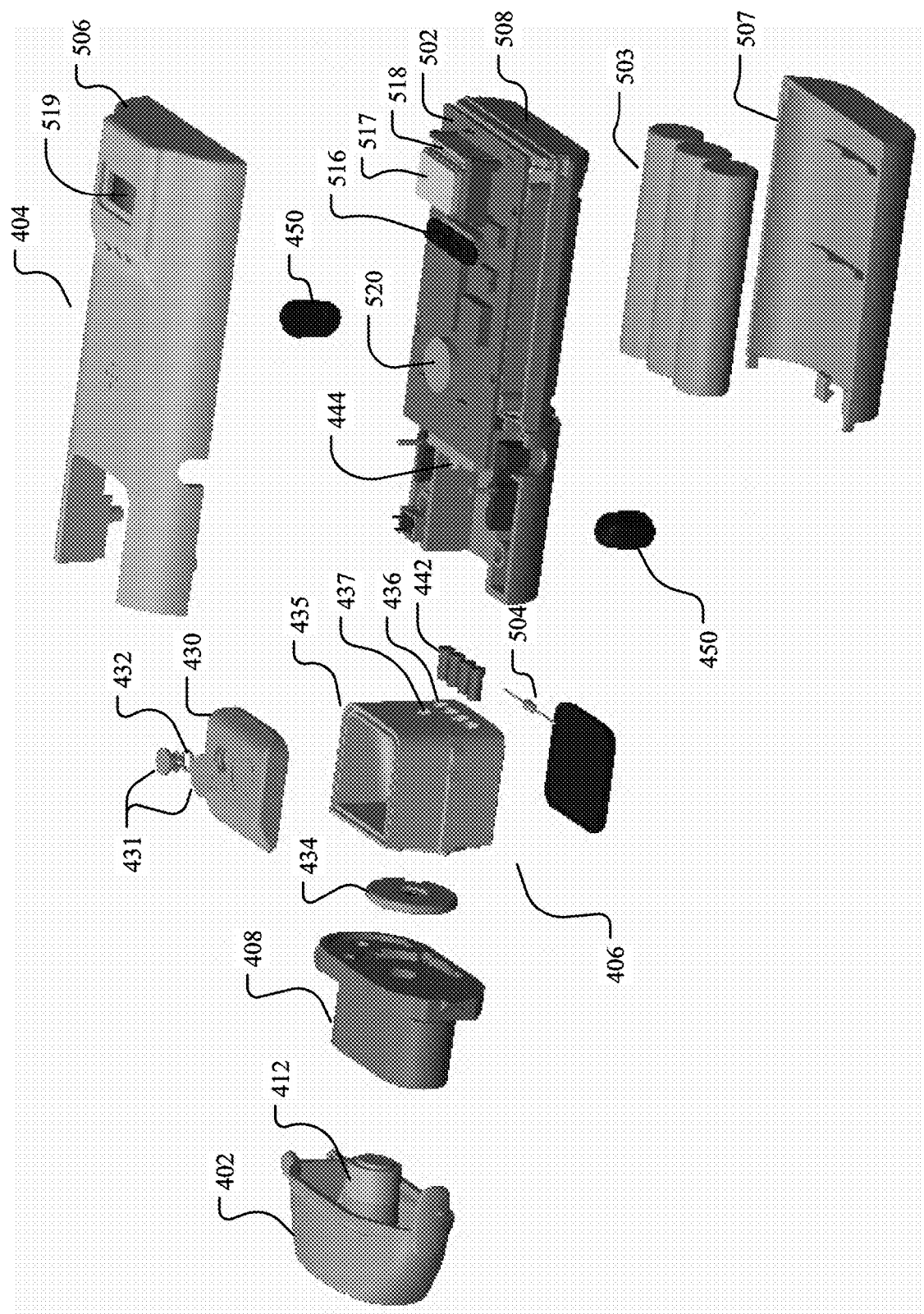

FIG. 1 illustrates an exemplary nasal droplet delivery device of the disclosure, showing a nasal droplet delivery device 100 having a nosepiece cover 102 in the open position. As shown, the droplet delivery device is configured in an in-line orientation in that the housing, its internal components, and various device components (e.g., the nosepiece, air inlet flow element, etc.) are orientated in a substantially in-line or parallel configuration (e.g., along the airflow path) so as to form a small, hand-held device.

In the embodiment shown in FIG. 1, the nasal droplet delivery device 100 includes a base unit 104 and a drug delivery ampoule 106. As illustrated in this embodiment, and discussed in further detail herein, the drug delivery ampoule 106 slides into the top of the base unit 104. In certain embodiments, nosepiece cover 102 may include a push element 102*a* that facilitates insertion of drug delivery ampoule 106. Also illustrated are one or more airflow entrances or openings 110. By way of example, there may be airflow entrances on the opposite side of the device, multiple airflow entrances on the same side of the device, or a combination thereof (not shown). The nasal droplet delivery device 100 also includes nosepiece 108 at the airflow exit side of the device.

With reference to FIG. 2, an exploded view of the exemplary nasal droplet delivery device 100 of FIG. 1 is shown, including internal components of the housing including a power/activation button 222; an electronics circuit board 218; a drug delivery ampoule 106 and fill plug 234 that comprises an ejector mechanism and reservoir (not shown); and a power source 216 (e.g., three AAA batteries, which may optionally be rechargeable) along with associated contacts 214. In certain embodiments, the reservoir may be single-unit dose or multi-unit dose that may be replaceable, disposable or reusable. Also shown, one or more pressure sensors 206 and optional spray sensors 204. In certain embodiments, the device may include cap 102, cap push 102*a*, cap lock 230, and ejector plate seal 232 to facilitate insertion and locking of drug delivery ampoule 106 into the base unit.

The components may be packaged in a housing, and generally oriented in an in-line configuration. The housing may be disposable or reusable, single-dose or multi-dose. Although various configurations to form the housing are within the scope of the disclosure, as illustrated in FIG. 2, the housing may comprise a top cover 228, a bottom cover 210, and an inner housing 202. The housing may also include a power source housing or cover 212.

In certain embodiments, the device may include audio and/or visual indications, e.g., to provide instructions and communications to a user. In such embodiments, the device may include a speaker or audio chip (not shown), one or more LED lights 2266, and LCD display 224 (interfaced with an LCD control board 220 and lens cover 236). The housing may be handheld and may be adapted for communication with other devices via a Bluetooth communication module or similar wireless communication module, e.g., for communication with a subject's smart phone, tablet or smart device (not shown).

With reference to FIG. 3, a cross-section of the nasal droplet delivery device 100 is shown further illustrating drug delivery ampoule 106 including reservoir 302 and ejector mechanism 304. In certain embodiments, an air inlet flow element 306 may also be positioned in the airflow at the airflow entrance of the housing and configured to facilitate non-turbulent (i.e., laminar and/or transitional) airflow across the exit side of aperture plate and to provide sufficient airflow to ensure that the ejected stream of droplets flows through the droplet delivery device during use. In some embodiments, the air inlet flow element may be positioned within the nosepiece. Aspects of the present embodiment further allows customizing the internal pressure resistance of the particle delivery device by allowing the placement of laminar flow elements having openings of different sizes and varying configurations to selectively increase or decrease internal pressure resistance, as will be explained in further detail herein.

In another embodiment, FIGS. 4A and 4B illustrate an alternative nasal droplet delivery device of the disclosure, with FIG. 4A showing the nasal droplet delivery device 400 with a base unit 404 having a nosepiece cover 402 in the closed position, and FIG. 4B with a base unit 404 having a nosepiece cover 402 in the open position. As shown, the nasal droplet delivery device is configured in an in-line orientation in that the housing, its internal components, and various device components (e.g., the nosepiece, air inlet flow element, etc.) are orientated in a substantially in-line or parallel configuration (e.g., along the airflow path) so as to form a small, hand-held device.

In the embodiment shown in FIGS. 4A and 4B, the nasal droplet delivery device 400 includes a base unit 404 and a drug delivery ampoule 406. As illustrated in this embodiment, and discussed in further detail herein, the drug delivery ampoule 406 slides into the front of the base unit 404. In certain embodiments, nosepiece cover 402 may include aperture plate plug 412. Also illustrated are one or more airflow entrances or openings 410 in nosepiece 408. By way of example, there may be airflow entrances on the opposite side of the device, multiple airflow entrances on the same side of the device, or a combination thereof (not shown). The nasal droplet delivery device 400 also includes nosepiece 408 at the airflow exit side of the device.

With reference to FIG. 5, an exploded view of the exemplary nasal droplet delivery device of FIGS. 4A and 4B is shown, including internal components of the housing including an electronics circuit board 502; a drug delivery ampoule 406 that comprises top cover 430 having optional vents 431 and vapor barriers 432, an ejector mechanism 434, a drug reservoir 435, electrical contacts 436, and one or more sensor ports 437; and a power source 503 (e.g., three AAA batteries, which may optionally be rechargeable). In certain embodiments, the device may also include various electrical contacts 442 and sensor ports 444 to facilitate activation of the device upon insertion of drug delivery ampoule 406 into the base unit 404. Likewise, in certain embodiments, the device may include resistors or chips 504 to facilitate insertion and detection of drug delivery ampoule 406 into the base unit 404.

In certain embodiments, the reservoir may be single-unit dose or multi-unit dose that may be replaceable, disposable or reusable. As illustrated in FIG. 5, in certain embodiments, the drug delivery ampoule may also comprise or be interfaced with a nosepiece 408 and a nosepiece cover 402. As shown, ejector mechanism 434 may be positioned in line with nosepiece 408 and drug reservoir 435 such that the exit side of the aperture plate is perpendicular to the direction of airflow and the stream of droplets is ejected in parallel to the direction of airflow. The nosepiece cover 402 may further include an aperture plate plug 412.

The components may be packaged in a housing, and generally oriented in an in-line configuration. The housing may be disposable or reusable, single-dose or multi-dose. Although various configurations to form the housing are within the scope of the disclosure, as illustrated in FIG. 5, the housing may comprise a top cover 506, a bottom cover 507, and an inner housing 508. The device may also include one or more ampoule release buttons 550, e.g., positioned on the side of the housing to facilitate release of the drug delivery ampoule 406 once inserted into the base unit 404.

In certain embodiments, the device may include audio and/or visual indications, e.g., to provide instructions and communications to a user. In such embodiments, the device may include a speaker or audio chip 520, one or more LED lights 516, and LCD display 517 (interfaced with an LCD control board 518 and lens cover 519). The housing may be handheld and may be adapted for communication with other devices via a Bluetooth communication module or similar wireless communication module, e.g., for communication with a subject's smart phone, tablet or smart device (not shown).

Figure 4:
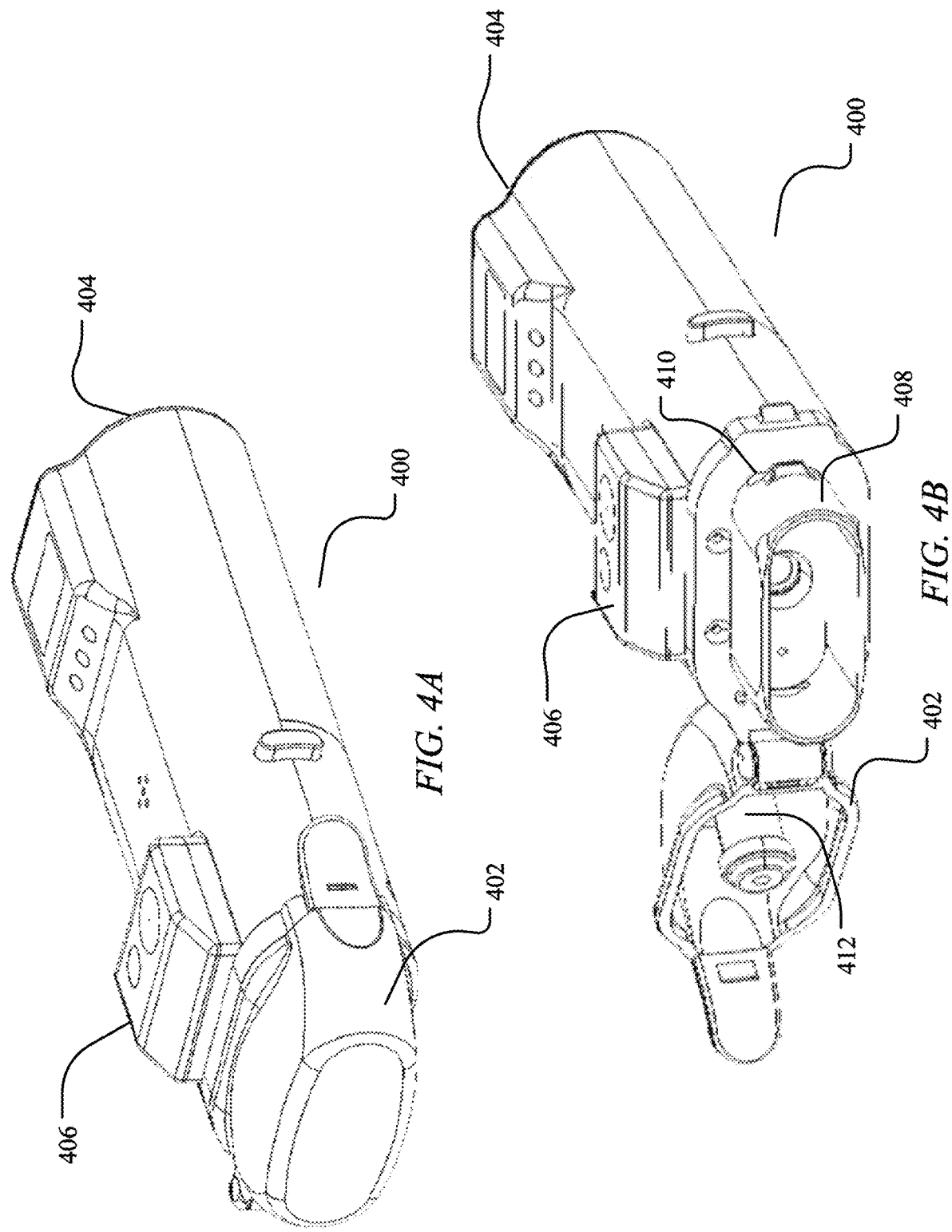
Figure 6:
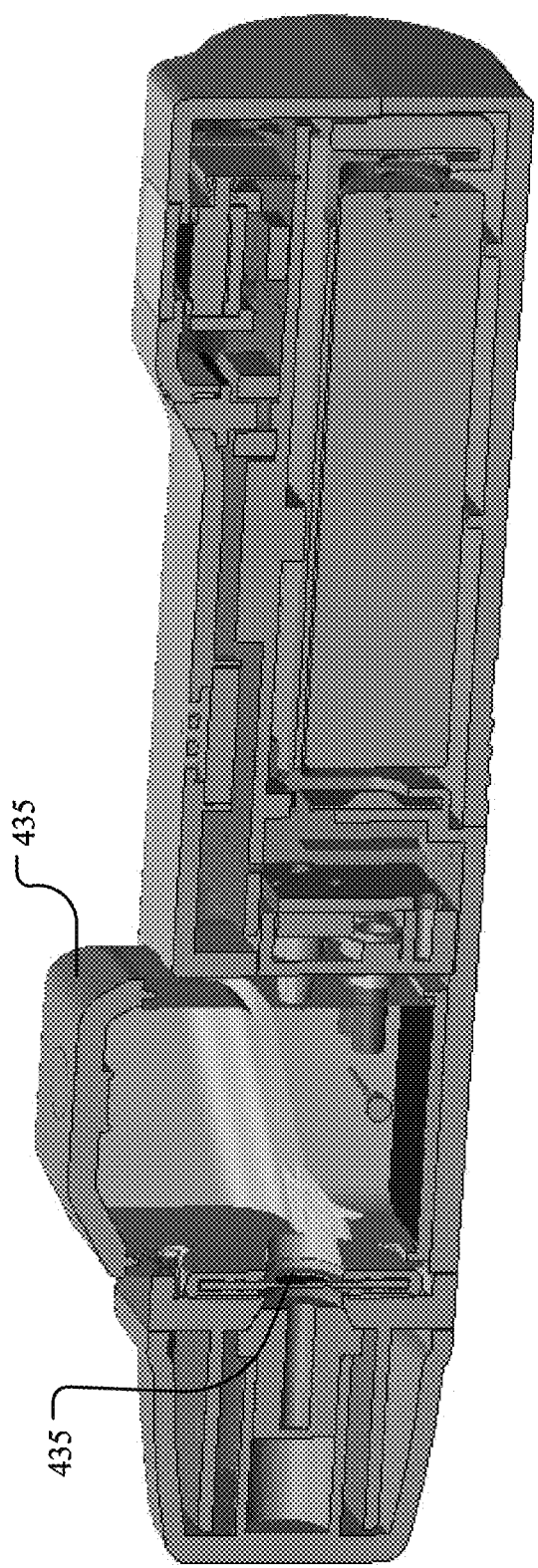

With reference to FIG. 6, a cross-section of a nasal device of FIGS. 4A and 4B is shown to illustrate an exemplary configuration of the interior of the drug reservoir 435 and its relation to ejector mechanism 434. As shown, drug reservoir 435 may be sized and shaped such that the volume of fluid held within the reservoir is funneled and directed to the ejection surface of the aperture plate during use. More particularly, as shown, the bottom surface of the drug reservoir may be sloped towards the ejector mechanism so as to facilitate flow of the fluid within the drug reservoir during use. Without intending to be limited by theory, such configurations may be particularly suited for device orientations wherein the ejector mechanism is oriented perpendicularly to the direction of airflow. However, it is noted that the disclosure is not so limited, and various shapes, sizes and configurations of ampoule are envisioned as within the scope of the disclosure.

Figure 7:
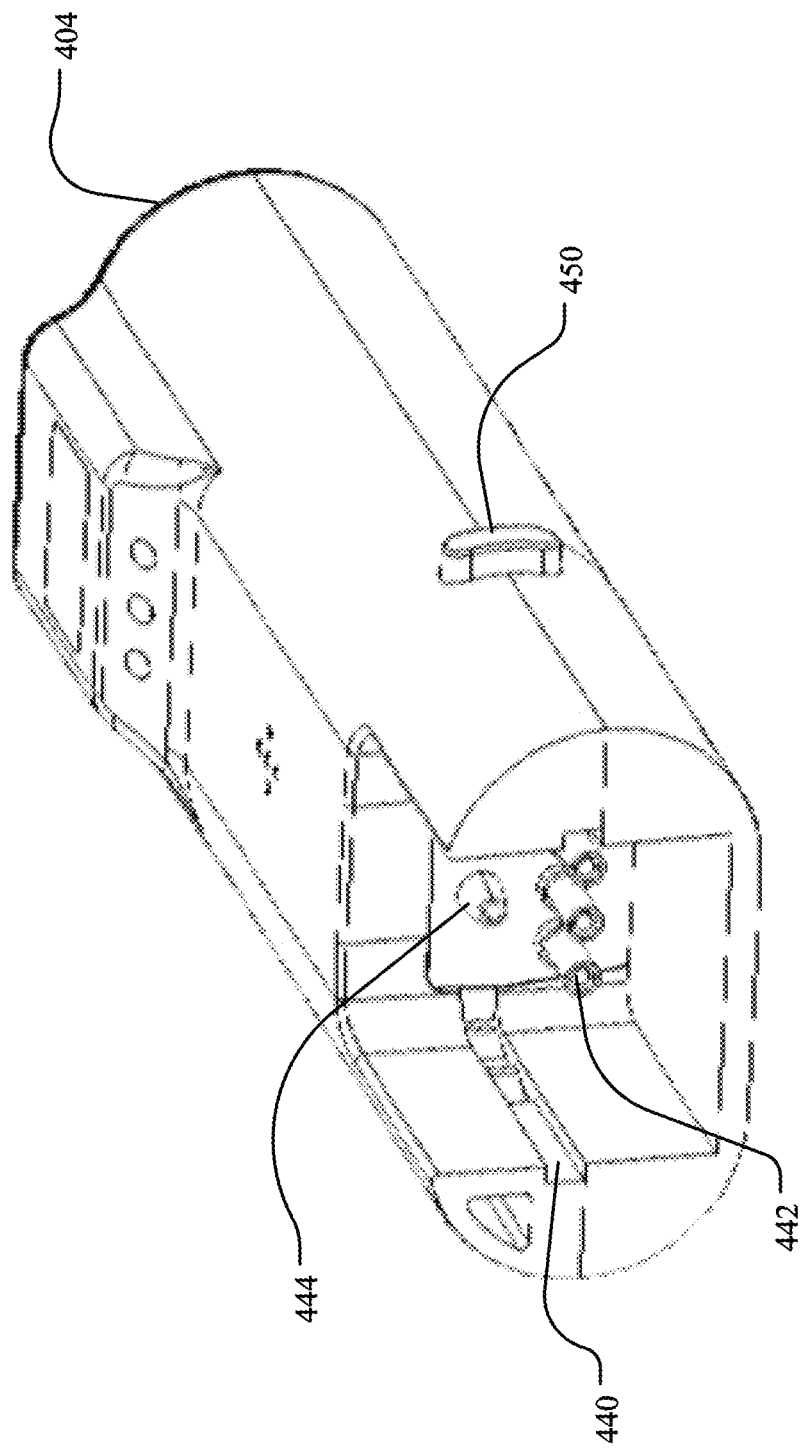

FIG. 7 illustrates the base unit 404 of the embodiment of FIGS. 4A and 4B without the drug delivery ampoule inserted. Without the drug delivery ampoule inserted, tracks 440 for directing the ampoule into place, electrical contacts 442, and sensor port 444 are shown. Also shown is release button 450.

Figure 8:
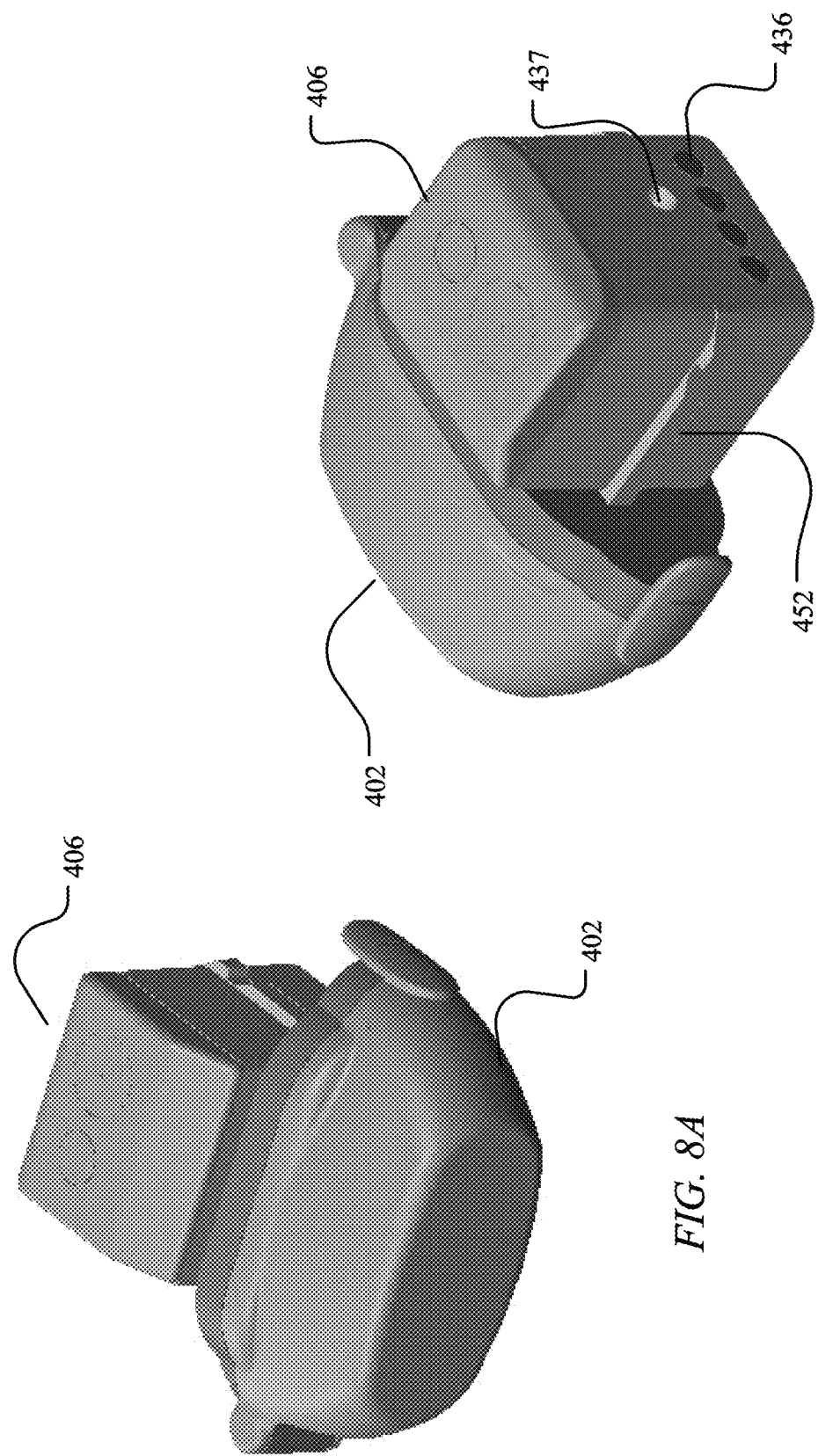

FIGS. 8A and 8B illustrate a drug delivery ampoule 406 with nosepiece cover 402 attached and in a closed position in front view (FIG. 8A) and back view (FIG. 8B). FIG. 8B illustrates electrical contacts 436 and sensor port 437 of the ampoule, as well as protruding slides 452 to facilitate placement of the ampoule into tracks 440 during insertion. By way of example with reference to FIG. 7, when drug delivery ampoule 406 is inserted into base unit 404, protruding slides 452 mate with tracks 440, sensor port 437 mates with sensor port 444, and electrical contacts 436 mates with electrical contacts 442. The drug delivery ampoule is pushed into the base unit and locked into place with the protruding slides and tracks engaging one another. During use, a pressure sensor located on the control board senses pressure changes within the device via the pressure sensing ports (e.g., within the nosepiece). To facilitate detection of pressure changes, the base unit includes a second pressure sensing port and outside channel (not shown) to facilitate sensing of reference or ambient pressure.

Figure 9:
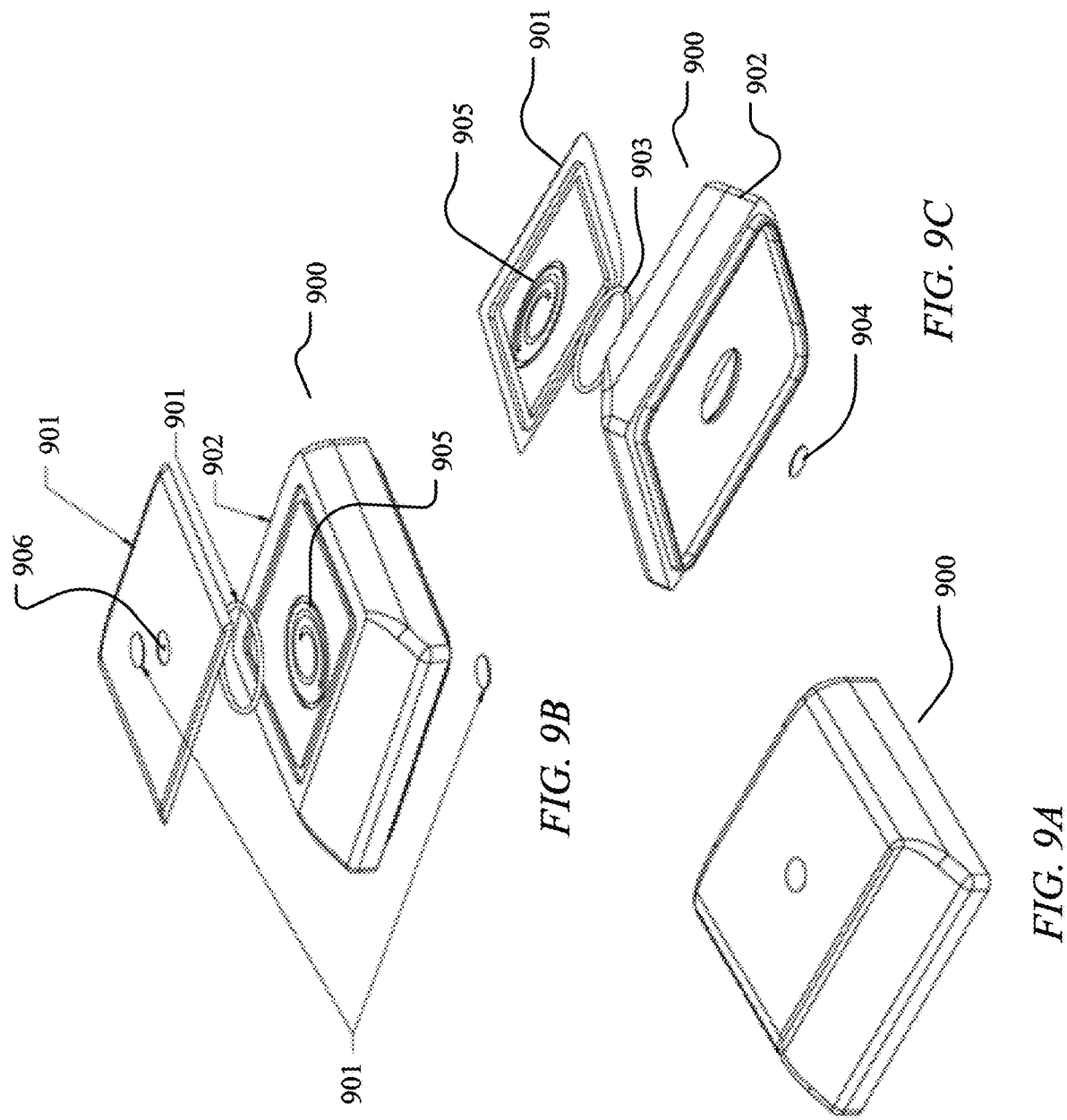

As discussed herein, the drug reservoir and/or drug delivery ampoule may include various vents and/or vapor barriers to facilitate venting, etc. With reference to FIGS. 9A-9C, an exemplary reservoir or ampoule is shown which is configured so as to be insensitive to pressure differentials that may occur when the user travels from sea level to sub-sea levels and at high altitudes, e.g., while traveling in an airplane where pressure differentials may be as great as 4 psi. As shown, FIG. 9A shows a perspective view of an exemplary ampoule 900. FIGS. 9B and 9C show exploded view of ampoule 900 from perspective top and bottom views. With reference to FIGS. 9B and 9C, the ampoule 900 generally includes a top cover 901 and a bottom cover 902. The ampoule 900 may be configured to include one or more superhydrophobic filter(s) 904 covering one or more vents 906, and the fluid reservoir housing may include a spiral channel (or similarly shaped) vapor barrier 905, which provides for free exchange of air into and out of the fluid reservoir, while blocking moisture or fluids from passing into the reservoir, thereby reducing or preventing fluid leakage or deposition on aperture plate surfaces. If desired, one or more O-rings 903, or similar sealing mechanism, may be used to form a seal between the top cover 901 and the bottom cover 902 in connection with the vapor barrier 905. Without intending to be limited, the superhydrophobic filter and vent may generally allow for the venting of air and equilibration of air pressure within the fluid reservoir, while maintaining a sterile environment within the fluid reservoir. The spiral channel vapor barrier will generally prevent the transfer of moisture to and from the fluid reservoir (e.g., through the vent opening).

Figure 10:
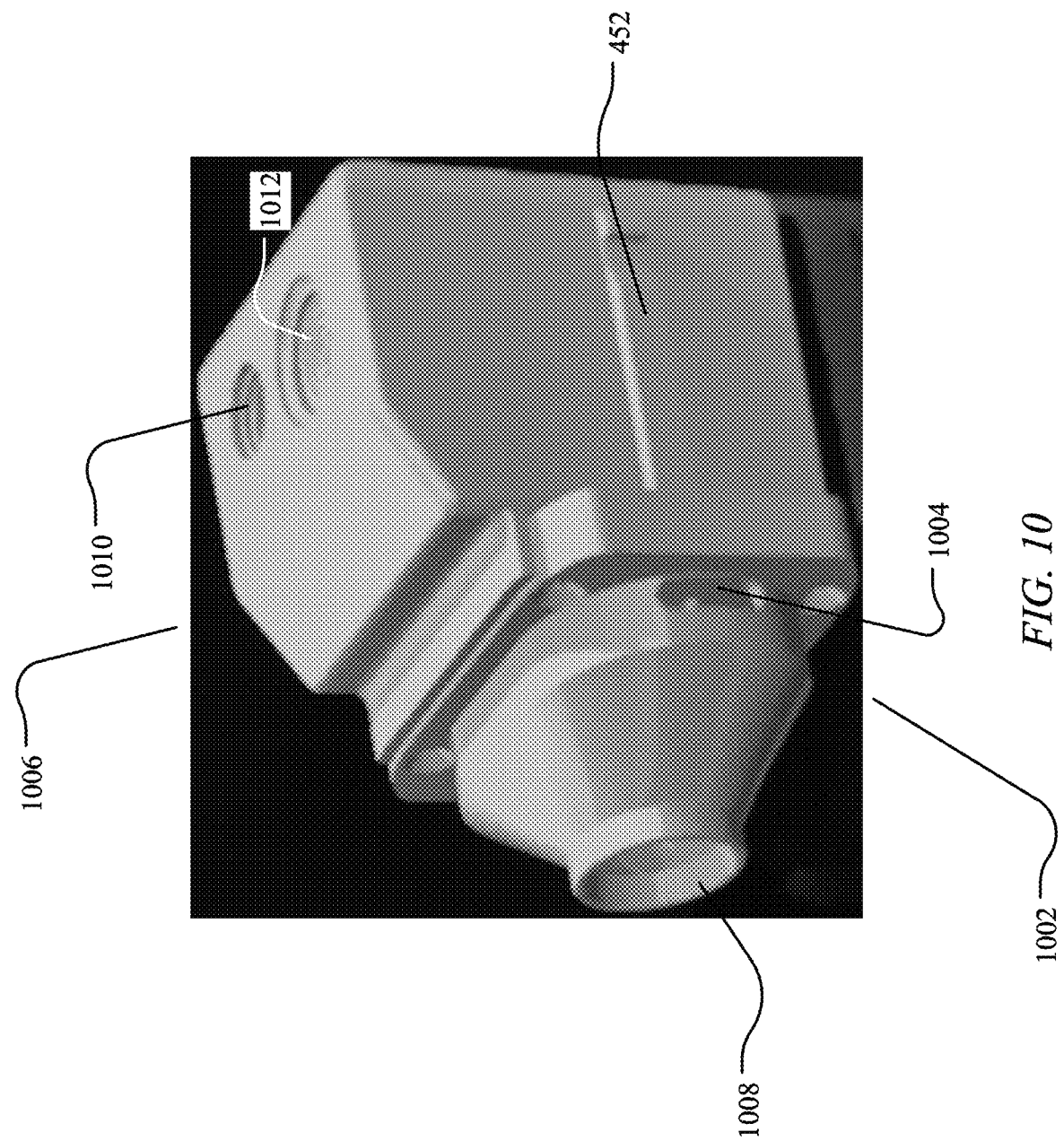

By way of example, FIG. 10 illustrates an exemplary drug delivery ampoule 1006 with a vent 1010 and vapor barrier 1012, and with nosepiece 1002 attached. As illustrated, nosepiece 1002 includes airflow entrances 1004 and airflow exit port 1008. Again, by way of example with reference to FIG. 7, when drug delivery ampoule 1006 is inserted into base unit 404, protruding slides 452 mate with tracks 440. The drug delivery ampoule is pushed into the base unit and locked into place with the protruding slides and tracks engaging one another.

Figure 11B:
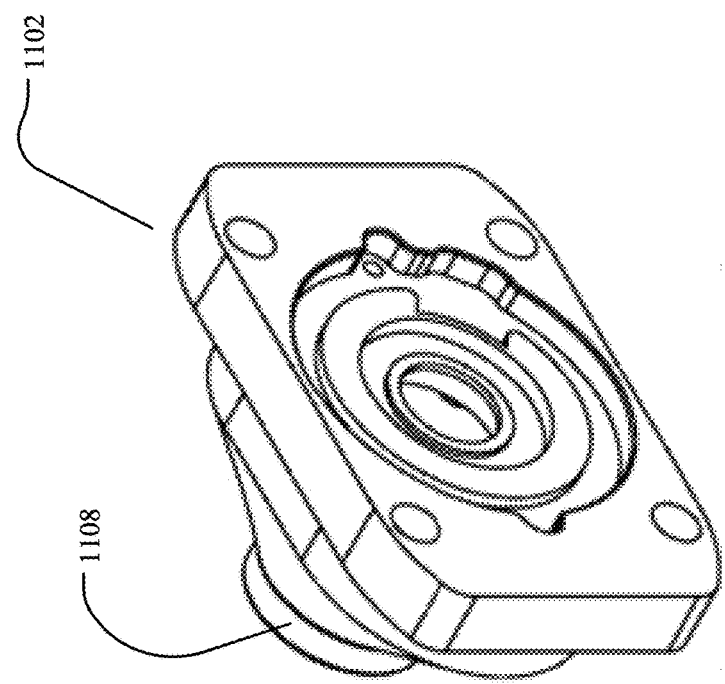
Figure 11A:
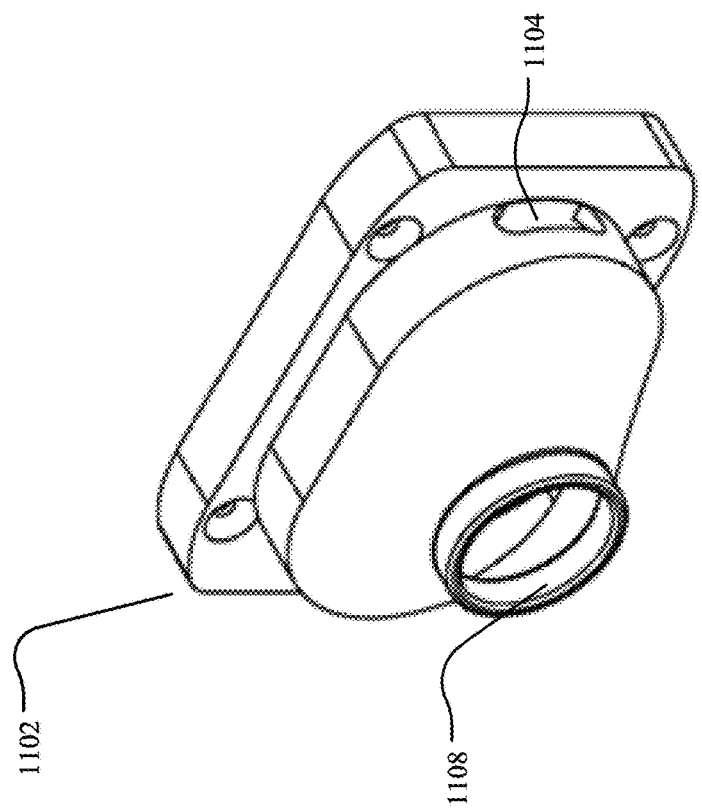

FIGS. 11A and 11B illustrate an exemplary nosepiece 1102 in front and rearview that may be attached to a drug delivery ampoule (not shown). Again, nosepiece 1102 includes airflow entrances 1104. The backside of the nosepiece (shown in FIG. 11B) may include various grooves and surfaces configured to accommodate device components, including the ejector mechanism and various sensors. Further, the nosepiece may include an air inlet flow element (not shown). As shown, the airflow exit port 1108 of nosepiece 1102 is generally circular. However, the disclosure is not so limited. The airflow exit port of the nosepiece through which the ejected plume of droplets exit as they are inhaled into a subject's nasal passageway, may be configured and have, without limitation, a cross sectional shape of a circle, oval, or other suitable shape, while the shape of the length of the tube, again without limitation, may be straight, curved or have a Venturi-type shape. In this regard, the airflow exit to the subject's nasal passageway may be configured to facilitate droplet flow while minimizing impingement of the droplets on the interior surface of the device.

Figure 3:
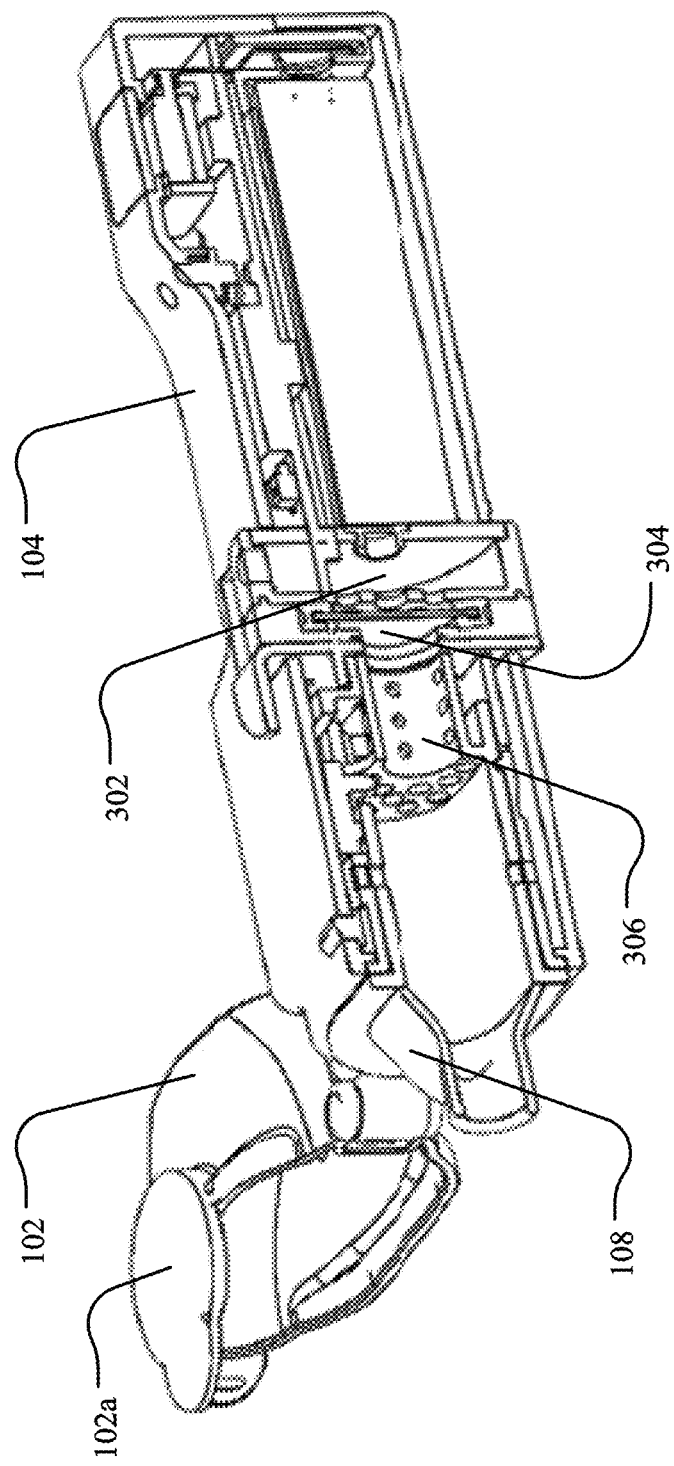

In one embodiment, the air inlet flow element may be located at the air entry side of the nosepiece (see, e.g., FIGS. 3 and 12) to facilitate laminar airflow across the exit side of aperture plate of the ejector mechanism and to provide sufficient airflow to ensure that the ejected plume of droplets flow through the device during use. Aspects of the present embodiment further allows customizing the internal pressure resistance of the droplet delivery device by allowing the placement of air inlet flow elements having openings of different sizes and varying configurations to selectively increase or decrease internal pressure resistance, as will be explained in further detail herein.

In accordance with certain embodiments of the nasal droplet delivery device of the disclosure, the device may include an air inlet flow element may be positioned in the airflow at the airflow entrance of the device and configured to facilitate non-turbulent (i.e., laminar and/or transitional) airflow across the exit side of aperture plate and to provide sufficient airflow to ensure that the ejected stream of droplets flows through the droplet delivery device during use. In some embodiments, the air inlet flow element may be positioned within the nosepiece. In addition, the air inlet flow element allows for customization of internal device pressure resistance by designing openings of different sizes and varying configurations to selectively increase or decrease internal pressure resistance.

As will be described in further detail herein, the air inlet flow element may be positioned behind the exit side of the aperture plate along the direction of airflow, or in-line or in front of the exit side of the aperture plate along the direction of airflow. In certain embodiments, the air inlet flow element comprises one or more openings formed there through and configured to increase or decrease internal pressure resistance within the droplet delivery device during use. For instance, the air inlet flow element comprises an array of one or openings. In the embodiments, the air inlet flow element comprises one or more interior baffles or substantially cylinder air flow elements, e.g., wherein the one or more baffles or cylinders comprise one or more airflow openings.

Figure 12:
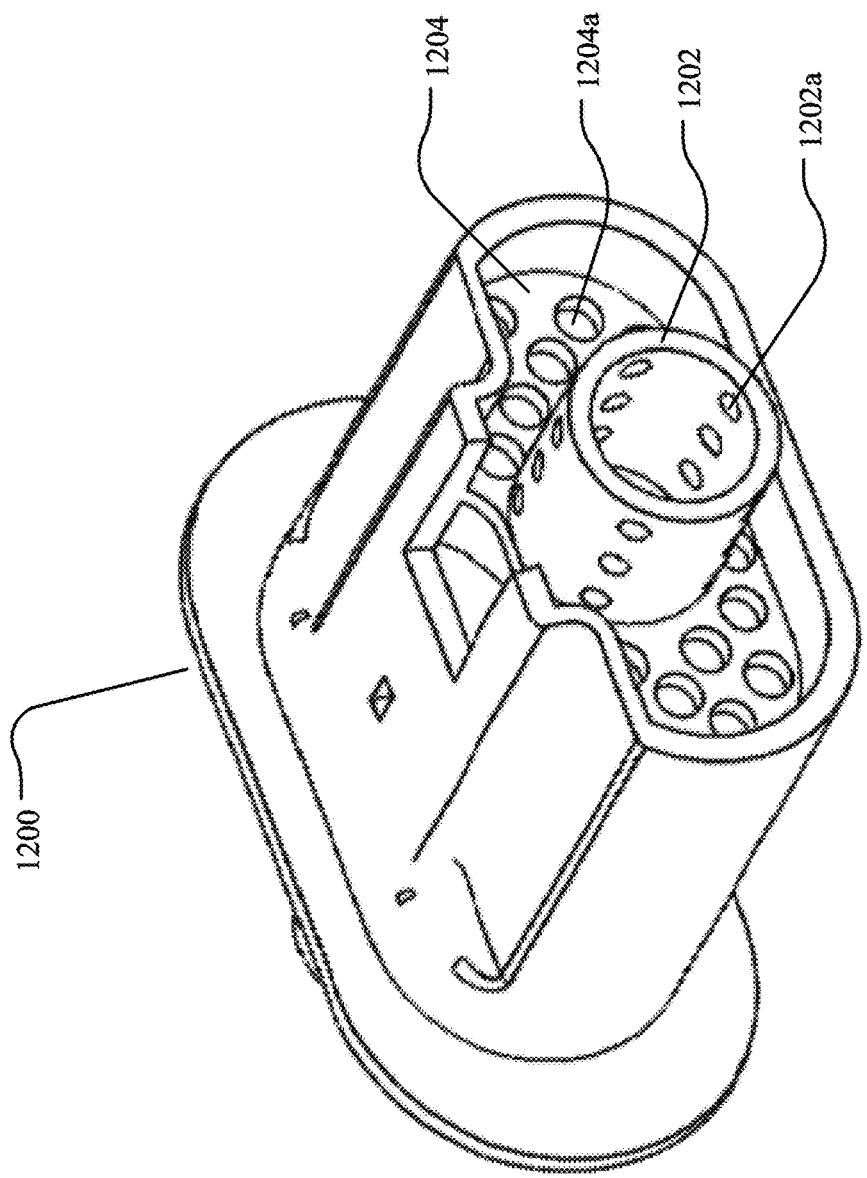

An exemplary nosepiece with air inlet flow element is shown in FIG. 12. The nosepiece may include an air inlet flow element 1200 comprising a substantially concentric baffle or cylinder baffle 1202 including one or more additional openings 1202a on its perimeter surfaced, the baffle positioned on planar array element 1204 having one or more openings 1204a, the air inlet flow element to provide resistance and modeling of airflow. The planar array element may be positioned in a perpendicular arrangement with the direction of airflow.

In certain embodiments, the air inlet flow element is designed and configured in order to provide an optimum airway resistance for achieving peak inspirational flows that are required for deep inhalation which promotes delivery of ejected droplets deep into the pulmonary airways. Air inlet flow elements also function to promote non-turbulent flow across the aerosol plume exit port, which also serves to stabilize airflow repeatability, stability and insures an optimal precision in the delivered dose.

Without intending to be limited by theory, in accordance with aspects of the disclosure, the size, number, shape and orientation of openings in the air inlet flow element of the disclosure may be configured to provide a desired pressure drop within the nasal droplet delivery device. In certain embodiments, it may be generally desirable to provide a pressure drop that is not so large as to strongly affect a user's inhalation or perception of inhalation.

In certain implementations, the use of air inlet flow elements having different sized openings, or the use of adjustable apertures may be required in order to accommodate the differences among inspiratory flow rates of young and old, small and large, and various disease states. For example, if the aperture is adjustable by the patient (perhaps by having a slotted ring that can be rotated), then a method may be provided to read the aperture hole setting and lock that position to avoid inadvertent changes of the aperture hole size, hence the flow measurement. Although pressure sensing is an accurate method for flow measurement, other embodiments may use, e.g., hot wires or thermistor types of flow rate measurement methods which lose heat at a rate proportional to flow rate, moving blades (turbine flow meter technology) or by using a spring-loaded plate, without limitation of example.

In certain embodiments, as illustrated herein, the reservoir/cartridge module may include components that may carry information read by the housing electronics including key parameters such as ejector mechanism functionality, drug identification, and information pertaining to patient dosing intervals. Some information may be added to the module at the factory, and some may be added at the pharmacy. In certain embodiments, information placed by the factory may be protected from modification by the pharmacy. The module information may be carried as a printed barcode or physical barcode encoded into the module geometry (such as light transmitting holes on a flange which are read by sensors on the housing). Information may also be carried by a programmable or non-programmable microchip on the module which communicates to the electronics in the housing.

By way of example, module programming at the factory or pharmacy may include a drug code which may be read by the device, communicated via Bluetooth to an associated user smartphone and then verified as correct for the user. In the event a user inserts an incorrect, generic, damaged, etc., module into the device, the smartphone might be prompted to lock out operation of the device, thus providing a measure of user safety and security not possible with passive inhaler devices. In other embodiments, the device electronics can restrict use to a limited time period (perhaps a day, or weeks or months) to avoid issues related to drug aging or build-up of contamination or particulates within the device housing.

The nasal droplet delivery device may further include various sensors and detectors to facilitate device activation, spray verification, patient compliance, diagnostic mechanisms, or as part of a larger network for data storage, big data analytics and for interacting and interconnected devices used for subject care and treatment, as described further herein. Further, the housing may include an LED assembly on a surface thereof to indicate various status notifications, e.g., ON/READY, ERROR, etc.

In another embodiment (not shown), a mini fan or centrifugal blower may be located at the air inlet side of the laminar flow element or internally of the housing within the airsteam. The mini fan generally may provide additional airflow and pressure to the output of the plume. For patients with low inspiratory flow, this additional airplume may ensure that the plume of droplets is pushed through the device into the patient's nasal passageway. In certain implementations, this additional source of airflow ensures that the plume exit port is swept clean of the droplets and also provides mechanism for spreading the particle plume into an airflow which creates greater separation between droplets. The airflow provided by the mini fan may also act as a carrier gas, ensuring adequate dose dilution and delivery.

In other embodiments, the internal pressure resistance of the nasal droplet delivery device may be customized to an individual user or user group by modifying the nosepiece tube design to include various configurations of air aperture grids or openings, thereby increasing or decreasing resistance to airflow through the device as the user inhales. For instance, different air entrance aperture sizes and numbers may be used to achieve different resistance values, and thereby different internal device pressure values. This feature provides a mechanism to easily and quickly adapt and customize the airway resistance of the particle delivery device to the individual patient's state of health or condition.

In another aspect of the disclosure, in certain embodiments, the nasal droplet delivery devices provide for various automation, monitoring and diagnostic functions. By way of example, as described above, device actuation may be provided by way of automatic subject breath actuation. Further, in certain embodiments, the device may provide automatic spray verification, to ensure that the device has generated the proper particle generation and provided to proper dosing to the subject. In this regard, the particle delivery device may be provided with one or more sensors to facilitate such functionality.

For instance, an airflow sensor located in the nosepiece may measure inspiratory and expiratory flow rates. This sensor is placed so that it does not interfere with drug delivery or become a site for collection of residue or promote bacterial growth or contamination. A differential (or gage) pressure sensor downplume of a flow restrictor (e.g., air inlet flow element) measures airflow based upon the pressure differential between the inside of the nosepiece relative to the outside air pressure. During inhalation (inspiratory flow) the nosepiece pressure will be lower than the ambient pressure and during exhalation (expiratory flow) the nosepiece pressure will be greater than the ambient pressure. The magnitude of the pressure differential during an inspiratory cycle is a measure of the magnitude of airflow and airway resistance at the air inlet end of the delivery tube.

Again, a Bluetooth communication module or similar wireless communication module may be provided in order to link the droplet delivery device to a smartphone or other similar smart devices (not shown). Bluetooth connectivity facilitates implementation of various software or App's which may provide and facilitate patient training on the use of the device. A major obstacle to effective inhaler drug therapy has been either poor patient adherence to prescribed aerosol therapy or errors in the use of an inhaler device. By providing a real time display on the smartphone screen of a plot of the patient's inspiratory cycle, (flow rate versus time) and total volume, the patient may be challenged to reach a goal of total inspiratory volume that was previously established and recorded on the smartphone during a training session in a doctor's office. Bluetooth connectivity further facilitates patient adherence to prescribed drug therapy and promotes compliance by providing a means of storing and archiving compliance information, or diagnostic data (either on the smartphone or cloud or other large network of data storage) that may be used for patient care and treatment.

More specifically, in certain embodiments, the droplet delivery device may provide automatic spray verification via LED and photodetector mechanisms. For instance, an infra-red transmitter (e.g., IR LED, or UV LED<280 nm LED), and infra-red or UV (UV with <280 nm cutoff) photodetector may be mounted along the droplet ejection side of the device to transmit an infra-red or UV beam or pulse, which detects the plume of droplets and thereby may be used for spray detection and verification. The IR or UV signal interacts with the aerosol plume and can be used to verify that a plume of droplets has been ejected as well as provide a measure of the corresponding ejected dose of medicament. Examples include but not limited to, infrared 850 nm emitters with narrow viewing angles of either, 8, 10 and 12-degrees, (MTE2087 series) or 275 nm UV LED with a GaN photodetector for aerosol plume verification in the solar blind region of the spectra. Alternatively in some applications, the sub 280 nm LEDs (e.g. 260 nm LEDs) can be used to disinfect the housing.

By way of example, the concentration of a medicament in the ejected fluid may be made, according to Beer's Law Equation (Absorbance=eLc), where, e is the molar absorptivity coefficient (or molar extinction coefficient) which is a constant that is associated with a specific compound or formulation, L is the path length or distance between LED emitter and photodetector, and c is the concentration of the solution. This implementation provides a measure of drug concentration and can be used for verification and a means and way to monitoring patient compliance as well as to detect the successful delivery of medication.

In another embodiment, spray verification and dose verification can be monitored by measuring the transmission of 850 nM to 950 nM light across the spray in a region where the droplets are not variably diluted with different inhalation flow rates. The average and alternating signals from the detector may be measured to calibrate and confirm the optical path (average signal) and detect the spray (alternating signal). In practice, the alternating signal can be measured by a 100 Hz low-pass filter between the detector and analog converter, sampling the signal 100 to 500 times a second, calculating the average and the range (maximum minus minimum) over 100 mS periods, and comparing these values to preset values to confirm proper operation and whether there was spray or not.

This method has the strong advantages of: low power consumption (less than 1 ma to the emitter); unaffected by stray light (visible light blocking on the detector); relatively resistant to digital noise or the 100 kHz piezo drive by the 100 Hz low-pass filter; the average signal level can be used to adjust the optical path for attenuation caused by drug deposits on the LED or detector; and simple hardware with a positive signal that is robustly measured.

This system also allows simple regulation of the optical signal strength by increasing power to the emitter should the average signal level decrease. Practically, this means using pulse width modulation of emitter current to regulate average emitter power. The pulses should be at a high rate, e.g., 100 kHz, so that this noise can be removed by the 100 Hz low pass filter. Nominal operation might use a 10% duty cycle of 10 mA to achieve and average current of 1 mA. This system would have the ability to increase the average current to 10 mA and correct for up to a factor of 10 attenuation by drug deposits.

In operation with the 950 nM emitter and detector having angles of +−20 degrees and spaced 10 mm apart. With 0.5 mA emitter power, a 10K collector resistor and 100 Hz low-pass filter, the average signal output is 2 volts and the peak to peak value of the alternating component is 4 mV without spray and 40 mV during spray. Without intending to be limited, in practice, there may be a transient large peak to peak value when the spray begins and ends as the bulk attenuation causes a large shift. The resistor sizing here is for continuous running of the emitter and not PWM.

In another embodiment, spray verification and dose verification can be monitored by measuring the transmission of 850 nM to 950 nM light across the spray in a region where the droplets are not variably diluted with different inhalation flow rates. The average and alternating signals from the detector may be measured to calibrate and confirm the optical path (average signal) and detect the spray (alternating signal). In practice, the alternating signal can be measured by a 100 Hz low-pass filter between the detector and analog converter, sampling the signal 100 to 500 times a second, calculating the average and the range (maximum minus minimum) over 100 mS periods, and comparing these values to preset values to confirm proper operation and whether there was spray or not.

This method has the strong advantages of: low power consumption (less than 1 ma to the emitter); unaffected by stray light (visible light blocking on the detector); relatively resistant to digital noise or the 100 kHz piezo drive by the 100 Hz low-pass filter; the average signal level can be used to adjust the optical path for attenuation caused by drug deposits on the LED or detector; and simple hardware with a positive signal that is robustly measured.

This system also allows simple regulation of the optical signal strength by increasing power to the emitter should the average signal level decrease. Practically, this means using pulse width modulation of emitter current to regulate average emitter power. The pulses should be at a high rate, e.g., 100 kHz, so that this noise can be removed by the 100 Hz low pass filter. Nominal operation might use a 10% duty cycle of 10 mA to achieve and average current of 1 mA. This system would have the ability to increase the average current to 10 mA and correct for up to a factor of 10 attenuation by drug deposits.

In operation with the 950 nM emitter and detector having angles of +-20 degrees and spaced 10 mm apart. With 0.5 mA emitter power, a 10K collector resistor and 100 Hz low-pass filter, the average signal output is 2 volts and the peak to peak value of the alternating component is 4 mV without spray and 40 mV during spray. Without intending to be limited, in practice, there may be a transient large peak to peak value when the spray begins and ends as the bulk attenuation causes a large shift. The resistor sizing here is for continuous running of the emitter and not PWM.

Yet another implementation of the disclosure includes and provides for a method for spray verification systems for detecting pressure differentials between the interior and exterior areas of the housing airflow region for verification of aerosol spray and drug delivery. In certain implementations, this signal provided by the pressure sensors provides a trigger for activation of a spray at or during a peak period of a patient's inhalation cycle and assures optimum deposition of the aerosol spray and drug delivery into the nasal passageways and sinus cavities.

Another implementation of the disclosure includes and provides a system and methods for an infrared LED (e.g. 850 nm) and an infrared photodetector for spray verification. Yet another implementation discloses and provides a system and methods of spray verification by using 'solar blind' photo detectors and UV-C LED's with peak emission wavelength below 280 nm and not limited by example, for measuring and sensing in either transmission or backscattering modes to detect the presence and quantity of ejected medication. The system can also be capable of operating in the fluorescence mode where the air stream is exposed to an energy source such as ultra violet light and substances in the air stream fluoresce, emitting photons of light having a specific wavelength. These systems and methods can be used to detect and measure a variety of airborne substances. These systems and methods provide a means of spray verification with maximum detection and provide assurance of elimination of incorrect or faulty detection of spray. The novel solar blind systems and methods provide greater flexibility of use and operation of the device with no interference when outdoors, in bright sunlight.

Still another implementation of the disclosure includes and provides a system and methods for spray verification by providing an audio signal when a dose is either dispensed by the breath actuation, and/or when an aerosol stream of droplets are detected. The addition of a sound chip to the electronics board, with a speaker, provides immediate feedback to the patient when a dose is successfully delivered. By providing real time feedback, the audio signal may maximize patient compliance by providing assurance that the dose was successfully delivered.

And another implementation of the disclosure includes and provides for a method for spray verification systems for measuring and quantifying the amount of drug ejected during ejection and nebulization. Absorbance of a nebulized drug dose may be provided by measuring the absorbance of light. In certain implementations the drug solution was previously calibrated using known concentrations to provide the drug's absorbance values at specified wavelengths. These systems and methods provide a means of providing verification that the drug was nebulized and ejected as well as provide the quantity and amount of drug in the ejected aerosol stream and the amount of drug remaining in the reservoir.

As previously stated, in the preferred embodiment, a pressure sensor (e.g., delta P sensor) is used to measure the airflow by measuring the pressure drop between the interior of the device and the surrounding atmosphere. Flow rate in milliliters per second, (or standard liters per minute (SLM)), is calculated from the measured pressure drop between the delta P sensor ports; one located upstream in the device aerosol delivery tube, near the air inlet port, in the vicinity of the air inlet flow element, while the second delta P sensor port measures ambient pressure outside the device. This measurement is also used to trigger the beginning and ending of an ejection cycle of droplets in order to coordinate the optimum point of the inhalation cycle with ejection and spray of the aerosol plume. The pressure measurement subsystem also differentiates between inhalation and exhalation so that droplet particles are only dispensed on inhalation during the inspiratory cycle.

In the present embodiment, the optical aerosol sensors measure and detect the presence of droplets by detecting light emitted from an LED source placed across the diameter of the inhalation tube and detecting the light scattered or absorbed by the droplets by a photodetector. The light source is a narrow viewing angle (<8 degrees) LED or a laser diode. In addition, multiple light sources and multiple detectors may be used to provide the shape of the aerosol plume so that the ejected mass can be better estimated. By measuring the cross section and length of the aerosol plume, there is higher confidence in the optical verification. These multiple light sources and multiple detectors may be placed either along the device aerosol exit port or in from of the ejector plate.

For example, for a device with a flow tube having an average diameter of 20 mm, a four-second inhalation of air from 100 milliliters to 500 mL will have an average velocity of from 8 to 40 centimeters per second. With the optical sensor located 20 mm downstream from the ejector, the front edge of the aerosol particles will arrive at the optical detector from 50 to 250 milliseconds after ejection.

Typical photodetectors which may be used in this application have response times of less than 1 millisecond, thus allowing accurate resolution of entrained droplet velocity. A second LED/photodetector system may be added and used to provide finer resolution of aerosol velocity. In the present embodiment the systems and methods provide for measuring and detecting the arrival of the aerosol plume at two downstream points, several centimeters apart. In this case, the LED source for each system is pulsed and synchronous detection (as is known in the engineering art) is used so synchronize each detector with its associated light source.

In addition, an image capture device, including cameras, scanners, or other sensors without limitation, e.g. charge coupled device (CCD), may be provided to detect and measure the ejected aerosol plume. These detectors, LED, delta P transducer, CCD device, all provide controlling signals to a microprocessor or controller in the device used for monitoring, sensing, measuring and controlling the ejection of a plume of droplets and reporting patient compliance, treatment times, dosage, and patient usage history, etc., via Bluetooth, for example.

In certain aspects of the disclosure, the ejector mechanism, reservoir, and housing/nosepiece function to generate a plume with droplet diameters less than about 5 um. As discussed above, in certain embodiments, the reservoir and ejector mechanism modules are powered by electronics in the device housing and a reservoir which may carry sufficient drug for a single dose, just a few doses, or several hundred doses of medicament.

In certain embodiments, as illustrated herein, the reservoir/cartridge module may include components that may carry information read by the housing electronics including key parameters such as ejector mechanism functionality, drug identification, and information pertaining to patient dosing intervals. Some information may be added to the module at the factory, and some may be added at the pharmacy. In certain embodiments, information placed by the factory may be protected from modification by the pharmacy. The module information may be carried as a printed barcode or physical barcode encoded into the module geometry (such as light transmitting holes on a flange which are read by sensors on the housing). Information may also be carried by a programmable or non-programmable microchip on the module which communicates to the electronics in the housing.

By way of example, module programming at the factory or pharmacy may include a drug code which may be read by the device, communicated via Bluetooth to an associated user smartphone and then verified as correct for the user. In the event a user inserts an incorrect, generic, damaged, etc., module into the device, the smartphone might be prompted to lock out operation of the device, thus providing a measure of user safety and security not possible with passive inhaler devices. In other embodiments, the device electronics can restrict use to a limited time period (perhaps a day, or weeks or months) to avoid issues related to drug aging or build-up of contamination or particulates within the device housing.

All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed:

1. An automatically actuated nasal droplet delivery device for delivering a fluid as an ejected stream of droplets to the nasal passageways and sinus cavities of a subject, the device comprising:
    a housing;
    a nosepiece positioned at an airflow exit of the device;
    a reservoir disposed within or in fluid communication with the housing for receiving a volume of fluid;
    an electronically actuated ejector mechanism in fluid communication with the reservoir and configured to generate the ejected stream of droplets;
    at least one differential pressure sensor positioned within the housing, the at least one differential pressure sensor configured to activate the ejector mechanism upon sensing a pre-determined pressure change within the device to thereby generate the ejected stream of droplets;
    the ejector mechanism comprising an oscillation actuator and an aperture plate, the aperture plate having a plurality of openings formed through its thickness and the actuator operable to oscillate the aperture plate at a frequency to thereby generate the ejected stream of droplets; and
    a photodetector configured to measure an ejected dose of medicament in the ejected stream of droplets.

2. The droplet delivery device of claim 1, wherein the housing and ejector mechanism are oriented such that an exit side of the aperture plate is perpendicular to the direction of airflow and the stream of droplets is ejected in parallel to the direction of airflow.

3. The droplet delivery device of claim 1, wherein the housing and ejector mechanism are oriented such that an exit side of the aperture plate is parallel to the direction of airflow and the stream of droplets is ejected substantially perpendicularly to the direction of airflow such that the ejected stream of droplets is directed through the housing at an approximate 90 degree change of trajectory prior to expulsion from the housing.

4. The droplet delivery device of claim 1, wherein the aperture plate comprises a domed shape.

5. The droplet delivery device of claim 1, wherein the aperture plate is composed of a material selected from the group consisting of poly ether ether ketone (PEEK), polyimide, polyetherimide, polyvinylidine fluoride (PVDF), ultra-high molecular weight polyethylene (UHMWPE), nickel, nickel-cobalt, nickel-palladium, palladium, platinum, metal alloys thereof, and combinations thereof.

6. The droplet delivery device of claim 1, wherein one or more of the plurality of openings have different cross-sectional shapes or diameters to thereby provide ejected droplets having different average ejected droplet diameters.

7. The droplet delivery device of claim 1, wherein the nosepiece is removably coupled with the device.

8. The droplet delivery device of claim 1, wherein the reservoir is removably coupled with the housing.

9. The droplet delivery device of claim 1, wherein the reservoir is coupled to the ejector mechanism to form a combination reservoir/ejector mechanism module, and the combination reservoir/ejector mechanism module is removably coupled with the housing.

10. The droplet delivery device of claim 1, further comprising a wireless communication module.

11. A method for delivering a therapeutic agent as an ejected stream of droplets to the nasal passageways and sinus cavities of a subject for the treatment of a disease, disorder or condition, the method comprising:
    (a) generating an ejected stream of droplets via a droplet delivery device of claim 1; and
    (b) delivering the ejected stream of droplets to the nasal passageways and sinus cavities of the subject such that at least about 50% of the mass of the ejected stream of droplets is delivered into the nasal passageways and sinus cavities of the subject during use to thereby treat the disease, disorder or condition.

12. The method of claim 11, wherein the disease, disorder, or condition is a local nasal or sinus disease, disorder or condition.

13. The method of claim 11, wherein the disease, disorder, or condition is a system disease, disorder or condition.

14. The method of claim 11, further comprising proving feedback from the device of whether a dose is successfully administered.

15. The method of claim 11, further comprising measuring entrained droplet velocity of droplets in the ejected stream.

16. The device of claim 1, further comprising a sensor configured to measure entrained droplet velocity of droplets in the ejected stream.

17. The device of claim 2, further comprising a sensor configured to measure entrained droplet velocity of droplets in the ejected stream.

18. The device of claim 3, further comprising a sensor configured to measure entrained droplet velocity of droplets in the ejected stream.

19. The device of claim 6, further comprising a sensor configured to measure entrained droplet velocity of droplets in the ejected stream.

20. The device of claim 10, further comprising a sensor configured to measure entrained droplet velocity of droplets in the ejected stream.

* * * * *